(12) United States Patent
Wu et al.

(10) Patent No.: US 10,655,137 B2
(45) Date of Patent: May 19, 2020

(54) INFLUENZA MUCOSAL VACCINE COMPOSITION AND PREPARATION AND APPLICATION THEREOF

(71) Applicant: National Tsing Hua University, Hsinchu (TW)

(72) Inventors: Suh-Chin Wu, Hsinchu (TW); Shi-Wei Lin, Hsinchu (TW); Neos Tang, Hsinchu (TW); Ting-Hsung Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/053,967

(22) Filed: Aug. 3, 2018

(65) Prior Publication Data

US 2019/0225979 A1   Jul. 25, 2019

(30) Foreign Application Priority Data

Jan. 25, 2018 (TW) .............................. 107102763 A

(51) Int. Cl.
| | | |
|---|---|---|
| *A61K 39/145* | (2006.01) |
| *A61K 49/00* | (2006.01) |
| *A61K 39/12* | (2006.01) |
| *C12N 15/82* | (2006.01) |
| *C07K 16/10* | (2006.01) |
| *C07K 14/005* | (2006.01) |
| *A61P 31/16* | (2006.01) |
| *C07K 14/11* | (2006.01) |
| *C12N 7/02* | (2006.01) |
| *C07K 14/245* | (2006.01) |
| *A61K 39/00* | (2006.01) |

(52) U.S. Cl.
CPC .......... *C12N 15/8258* (2013.01); *A61K 39/12* (2013.01); *A61P 31/16* (2018.01); *C07K 14/005* (2013.01); *C07K 16/1018* (2013.01); *A61K 2039/543* (2013.01); *A61K 2039/552* (2013.01); *A61K 2039/6037* (2013.01); *C07K 14/11* (2013.01); *C07K 14/245* (2013.01); *C07K 2317/92* (2013.01); *C07K 2319/00* (2013.01); *C07K 2319/21* (2013.01); *C12N 7/02* (2013.01); *C12N 2760/16034* (2013.01); *C12N 2760/16134* (2013.01)

(58) Field of Classification Search
None
See application file for complete search history.

*Primary Examiner* — Rodney P Swartz
(74) *Attorney, Agent, or Firm* — WPAT, PC

(57) ABSTRACT

Provided is an influenza mucosal vaccine composition and preparation and application thereof. This composition contains an antigen fusion protein which includes an influenza virus antigen and a Type IIb heat-labile enterotoxin A subunit from *Escherichia coli*. Immunization with this antigen fusion protein induces cellular and humoral immune responses, including systemic and mucosal immune responses, against a specific influenza virus in a subject, and therefore protects the subject from viral infection.

19 Claims, 19 Drawing Sheets

Specification includes a Sequence Listing.

N —[ His-tag | H5HA | GCN4 | GS linker | LTIIb-A ]— C

FIG. 1A

N —[ H5HA | GCN4 | His-tag | GS linker | LTIIb-A ]— C

FIG. 1B

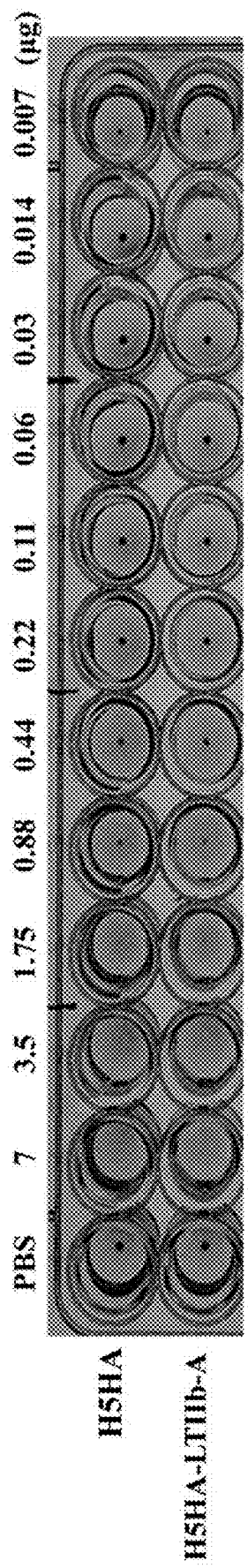
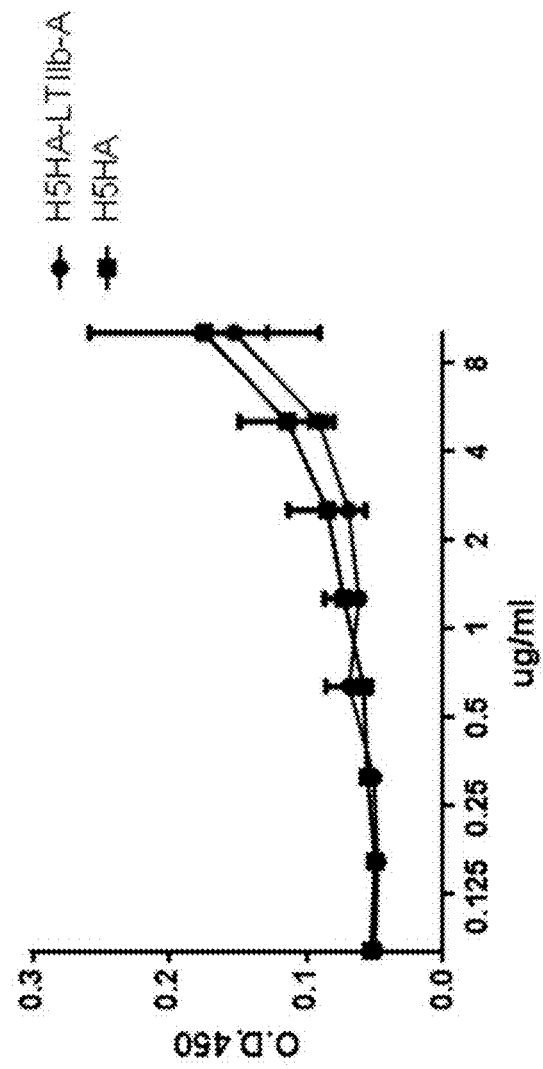
FIG. 2A
FIG. 2B

FIG. 5A

Serum neutralizing antibodies

- PBS
- H5HA
- H5HA-LTIIb-A
- H5HA-LTIIb-A+LTIIb-B5

FIG. 5B

BALF neutralizing antibodies

- PBS
- H5HA
- H5HA-LTIIb-A
- H5HA-LTIIb-A+LTIIb-B5

Spleen IL-4

- PBS
- H5HA
- H5HA-LTIIb-A
- H5HA-LTIIb-A+LTIIb-B5

FIG. 6C

CLNs IL-4

- PBS
- H5HA
- H5HA-LTIIb-A
- H5HA-LTIIb-A+LTIIb-B5

INFLUENZA MUCOSAL VACCINE COMPOSITION AND PREPARATION AND APPLICATION THEREOF

CROSS-REFERENCE TO RELATED APPLICATION

This application claims priority of Taiwan patent application No. 107102763, filed on Jan. 25, 2018, the content of which is incorporated herein in its entirety by reference.

BACKGROUND OF THE INVENTION

1. Field of the Invention

The present invention relates to a vaccine composition and preparation and application thereof. Particularly, the present invention relates to an influenza mucosal vaccine composition which utilizes an antigen fusion protein and the manufacture and application thereof.

2. The Prior Art

An influenza virus is an RNA virus belonging to the Orthomyxoviridae family. The influenza viruses that infect human include Type A, B, and C. The influenza A viruses have caused several pandemics in humans, including the Spanish flu caused by the H1N1 virus in 1918, the Asian flu caused by the H2N2 virus in 1957, and the global swine flu caused by the H1N1 virus in 2009.

The influenza A viruses that infect birds are designated as highly pathogenic avian influenza (HPAI) viruses, such as the H5N1 virus, or low pathogenic avian influenza (LPAI) viruses based on the severity of illness. HPAI viruses can infect humans through contact with diseased birds, with a high lethality in both birds and humans. The infection and replication of HPAI viruses in the human lower respiratory tract cause lung injuries and serum cytokine imbalance in patients, which leads to serious diseases. In 1997, a large number of chickens were killed due to H5N1 virus in Hong Kong chicken farms, and more than ten cases of human infections with H5N1 were reported. Since then, H5N1 avian flu has occurred in various parts of the world, including Asia, the Middle East, Europe and Africa.

To avoid the huge health and economic losses due to the flu, medical researchers have focused on the development of influenza vaccines, including mucosal vaccines that trigger mucosal immune responses in individuals. Mucosal vaccines may be administered via nasal, sublingual, oral, rectal, and vaginal routes, wherein intranasal vaccination induces mucosal and systemic immunity against the antigen and provides protection of the respiratory tract against foreign pathogens. However, intranasal vaccination usually requires assistance of adjuvants to elicit effective mucosal immunity. Common mucosal vaccine adjuvants include cholera toxin (CT), heat-labile enterotoxin (LT), unmethylated CpG dinucleotides, monophosphoryl lipid A (MPL), and Toll-like receptor stimulants.

Heat-labile enterotoxins are bacterial protein toxins, which are classified into the Type I and Type II subfamilies according to the amino acid sequence and specific binding to gangliosides. The Type II subfamily is further divided into three subgroups, including Type IIa, Type IIb, and Type IIc. The heat-labile enterotoxin consists of A and B subunits. The A subunit has the adenosine diphosphate (ADP)-ribosylating activity, and the B-subunit pentamer is able to bind glycoproteins on the surface of eukaryotic cells to enable the cell entry of enterotoxins. Because the action of the LT A subunit in cells reduces intestinal water absorption and leads to diarrhea, the LT-based vaccine adjuvants used in previous studies are usually the LT holotoxins containing a mutant A subunit or the pentamer of LT B subunit. There is lack of knowledge regarding preparing an effective influenza mucosal vaccine by a more simplified method, for example, constructing a single fusion protein by conjugating the wild-type LT A subunit with an influenza virus antigen.

SUMMARY OF THE INVENTION

As a result, the present invention provides an influenza mucosal vaccine composition which contains an antigen fusion protein, wherein the antigen fusion protein includes an influenza virus antigen and a Type IIb heat-labile enterotoxin A subunit from *Escherichia coli*.

In another aspect, the present invention provides a method of preventing influenza viral infection, including the step of administering to a subject in need an influenza mucosal vaccine composition which contains an antigen fusion protein, wherein the antigen fusion protein includes an influenza virus antigen and a Type IIb heat-labile enterotoxin A subunit from *E. coli*.

In one embodiment of the present invention, the influenza virus antigen of the antigen fusion protein is a hemagglutinin ectodomain; an N-terminal region of the antigen fusion protein further includes a poly-histidine segment; and the influenza mucosal vaccine composition may further contain a Type IIb heat-labile enterotoxin B subunit from *E. coli*, which is either separate from or conjugated with the antigen fusion protein.

In another embodiment of the present invention, the influenza mucosal vaccine composition contains 10 μg of the antigen fusion protein including the hemagglutinin ectodomain, and said composition is administered intranasally.

In still another embodiment of the present invention, the antigen fusion protein including an H5 hemagglutinin ectodomain activates Toll-like receptor 2/1 (TLR2/1) and induces T-cell related immune responses, such as the secretion of interferon-γ (IFN-γ), interleukin-4 (IL-4), interleukin-17A (IL-17A), or any combinations thereof.

In one further aspect, the present invention provides a method of preparing the abovementioned influenza mucosal vaccine composition, including the steps of: (a) preparing an antigen fusion protein which includes an influenza virus antigen and a Type IIb heat-labile enterotoxin A subunit from *E. coli*; and (b) mixing the antigen fusion protein with a pharmaceutically acceptable carrier to obtain the influenza mucosal vaccine composition.

In one embodiment of the present invention, the preparation method further includes adding a Type IIb heat-labile enterotoxin B subunit from *E. coli* to the influenza mucosal vaccine composition.

The influenza mucosal vaccine composition of the present invention utilizes a single antigen fusion protein to effectively elicit humoral and cellular immune responses against influenza viruses in a subject, for example, the production of influenza virus neutralizing antibodies in blood and bronchoalveolar mucosa and the various cytokines secreted by T cells to regulate innate and adaptive immune responses. Therefore, the influenza mucosal vaccine composition may enhance systemic and mucosal immunity against influenza viruses in a subject, prevent influenza virus entry into hosts via the respiratory tract, and reduce damages and even deaths caused by viral infection.

The present invention is further described in the following examples, in reference to the accompanying drawings. It should be understood that the examples given below do not limit the scope of the invention, and that modifications can be made without departing from the scope of the appended claims.

BRIEF DESCRIPTION OF THE DRAWINGS

FIG. 1A shows a construction scheme illustrating one embodiment of the present invention, an H5HA-LTIIb-A fusion protein, which includes an ectodomain of H5 hemagglutinin (hereinafter referred to as H5HA), a wild-type Type IIb heat-labile enterotoxin A subunit from E. coli (referred to as LTIIb-A), and an N-terminal poly-histidine tag;

FIG. 1B shows a construction scheme illustrating an H5HA-LTIIb-A fusion protein including a His-tag in the middle;

FIG. 2A shows comparison of hemagglutination due to the recombinant H5HA protein or the H5HA-LTIIb-A fusion protein by using hemagglutination assay;

FIG. 2B shows comparison of fetuin binding capability of the recombinant H5HA protein and the H5HA-LTIIb-A fusion protein by using fetuin binding assay;

FIG. 5A and FIG. 5B respectively show the neutralization curves of H5N1 influenza pseudovirus neutralizing antibodies in serum and BALF of BALB/c mice immunized with PBS, the recombinant H5HA protein, the H5HA-LTIIb-A fusion protein, or the combination of the H5HA-LTIIb-A fusion protein and the recombinant LTIIb-B5 protein;

FIG. 5C and FIG. 5D respectively show titers of H5N1 influenza pseudovirus neutralizing antibodies in serum and BALF of BALB/c mice immunized differently as indicated, and the titers were determined based on the data shown in FIG. 5A and FIG. 5B, respectively;

FIG. 6C and FIG. 6D respectively show the levels of IL-4 secreted by the stimulated T cells from spleen and CLNs of BALB/c mice immunized with PBS, the recombinant H5HA protein, the H5HA-LTIIb-A fusion protein, or the combination of the H5HA-LTIIb-A fusion protein and the recombinant LTIIb-B5 protein;

FIG. 7C shows the survival curves of BALB/c mice immunized with PBS, 5 μg of the recombinant H5HA protein, 5 μg of the H5HA-LTIIb-A fusion protein, or the combination of 5 μg of the H5HA-LTIIb-A fusion protein and 5 μg of the recombinant LTIIb-B5 protein, and then injected with H5N1 virus;

FIG. 7D shows the relative body weight of BALB/c mice immunized with PBS, 5 μg of the recombinant H5HA protein, 5 μg of the H5HA-LTIIb-A fusion protein, or the combination of 5 μg of the H5HA-LTIIb-A fusion protein and 5 μg of the recombinant LTIIb-B5 protein, and then injected with H5N1 virus;

FIG. 7E shows the survival curves of BALB/c mice immunized with PBS, 2.5 μg of the recombinant H5HA protein, 2.5 μg of the H5HA-LTIIb-A fusion protein, or the combination of 2.5 μg of the HSHA-LTIIb-A fusion protein and 5 μg of the recombinant LTIIb-B5 protein, and then injected with H5N1 virus;

FIG. 7F shows the relative body weight of BALB/c mice immunized with PBS, 2.5 μg of the recombinant HSHA protein, 2.5 μg of the HSHA-LTIIb-A fusion protein, or the combination of 2.5 μg of the HSHA-LTIIb-A fusion protein and 5 μg of the recombinant LTIIb-B5 protein, and then injected with H5N1 virus;

FIG. 10A shows the neutralization curves of H5N1 influenza virus neutralizing antibodies in serum of chick immunized with PBS, the recombinant HSHA protein, the HSHA-LTIIb-A fusion protein, or the combination of the HSHA-LTIIb-A fusion protein and the recombinant LTIIb-B5 protein; neutralization was measured by plaque reduction neutralization test (PRNT); and FIG. 10B shows titers of H5N1 influenza virus neutralizing antibodies in serum of chicks immunized differently as indicated, and the titers were determined based on the data shown in FIG. 10A.

DETAILED DESCRIPTION OF THE PREFERRED EMBODIMENT

Definition

Figure 1C:
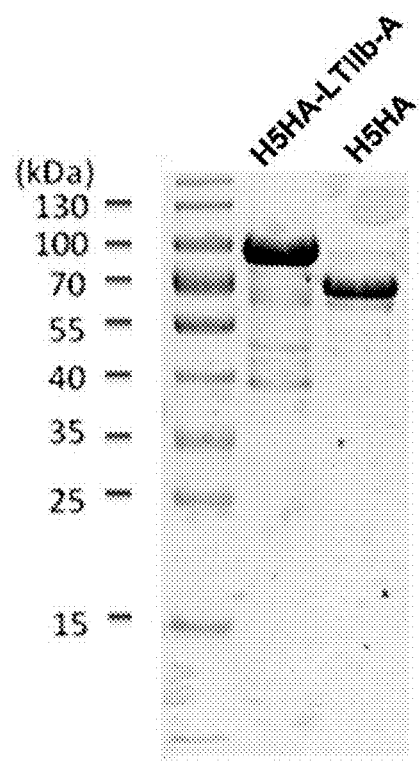
FIG. 1C shows an image of sodium dodecyl sulfate polyacrylamide gel electrophoresis (SDS-PAGE) verifying the production of the H5HA-LTIIb-A fusion protein and a recombinant H5HA protein.

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The term "HSHA" used herein is an abbreviation of H5 hemagglutinin ectodomain. The H5 hemagglutinin ectodomain is a domain located at the amino terminus (N-terminus) of the H5 hemagglutinin protein. H5 hemagglutinin also contains a transmembrane domain and a cytoplasmic tail located at the carboxyl terminus (C-terminus).

The expression "influenza virus antigen" used herein refers to any polypeptide, in full or partial length, that is derived from any type of influenza virus and is able to trigger immune responses in host animals, including mammals and birds. The immune responses triggered by the influenza virus antigen include activation of immune cells and production of cytokines and antigen-specific antibodies.

Materials and Methods

Preparation of the Recombinant Protein of H5 Hemagglutinin Ectodomain (H5HA)

Expression and purification of the recombinant protein of H5 hemagglutinin ectodomain were performed according to the method of Lin et al (Lin et al., PloS One, 2011; 6(5):e20052). The H5 hemagglutinin gene was derived from the complementary deoxyribonucleic acid (cDNA) of influenza A virus H5N1 subtype (A/Thailand/1 (KAN-1)/2004 strain). To avoid cleavage of the recombinant H5HA protein by protease, the nucleic acid sequence corresponding to the cleavage site in the H5HA gene fragment was slightly modified such that the amino acid sequence of the cleavage site was substituted from PQRERRRKKRG (SEQ ID NO: 1) to PQRETRG (SEQ ID NO: 2). The recombinant H5HA protein was expressed using the Bac-to-Bac insect baculovirus expression system (Invitrogen). Briefly, the modified H5HA gene fragment was cloned into a pFastbac.1 plasmid according to the manufacturer's instructions, and the plasmid was used to transform DH10Bac *E. coli*. The *E. coli* colonies carrying the baculovirus vector (bacmid) with the inserted H5HA gene fragment were picked by blue-white screening, and the bacmid was purified therefrom. Next, Sf9 insect cells (Invitrogen) were transfected with the bacmid for cell production of the baculovirus carrying the H5HA gene fragment, which was released into SF900 cell culture medium (Invitrogen). The baculovirus was added to Sf9 insect cells at a cell density of $2 \times 10^6$ cells/ml and incubated at 27° C. for 48 hours, allowing the cells to express and secrete the recombinant H5HA protein into SF900-II cell culture medium.

Preparation of the Recombinant Protein of *E. coli* Type IIb Heat-Labile Enterotoxin B Subunit (LTIIb-B5)

For expression of the pentameric recombinant LTIIb-B5 protein, LTIIb-B5 gene (SEQ ID NO: 3) from enterotoxigenic *Escherichia coli* (ETEC) was codon-optimized and cloned into a pET22b(+) vector to construct a LTIIb-B5-pET22b(+) plasmid. Next, *E. coli* BL21 cells (DE3) (Invitrogen) were transformed with the LTIIb-B5-pET22b(+) plasmid and cultured overnight at 37° C. in Luria-Bertani (LB) medium containing ampicillin. The overnight culture was inoculated into ampicillin-containing LB medium and incubated at 37° C. until an absorbance of 0.4-0.6 at 600 nm (OD 600) was reached, and an additional 4-hour incubation was carried out at 37° C. after isopropyl β-D-1-thiogalactopyranoside (IPTG) was added to induce the expression of recombinant LTIIb-B5 protein. Cell pellet was collected by centrifugation (10,000 rpm, 10 minutes, 4° C.).

For protein purification, the abovementioned cell pellet was resuspended in buffer A (300 mM Tris, 50 mM sodium chloride, 10 mM imidazole, 5% glycerol, pH 7.2) containing phenylmethane-sulfonyl fluoride (PMSF) and lysed at high pressure (15 Kpsi). The cell lysate was centrifuged at 10,000 rpm for 10 minutes at 4° C., and the pellet was collected and mixed with buffer A containing 8 M urea. The mixture was centrifuged at 10,000 rpm for 10 minutes at 4° C., and the supernatant was collected and mixed overnight with nickel-chelating resin (TOSOH). A column was packed with the resin mixture, washed with buffer A containing 0.5% Triton X-100, and eluted with 30-40% buffer B (300 mM Tris, 50 mM sodium chloride, 500 mM imidazole, 5% glycerol, pH 7.2-7.5) to obtain the recombinant LTIIb-B5 protein. The fractions of purified recombinant LTIIb-B5 protein were transferred to a dialysis bag with a 10 kDa molecular weight cut-off, dialyzed overnight at 4° C. against phosphate buffered saline (137 mM sodium chloride, 2.7 mM potassium chloride, 7.7 mM disodium hydrogen phosphate, 1.47 mM potassium dihydrogen phosphate, pH 7.4; referred to as PBS), concentrated by using a 10 kDa centrifuge tube (Millipore), and stored at −20° C. The recombinant LTIIb-B5 protein was identified by sodium dodecyl sulfate polyacrylamide gel electrophoresis (SDS-PAGE) and western blotting.

Sodium Dodecyl Sulfate Polyacrylamide Gel Electrophoresis (SDS-PAGE)

SDS-PAGE was performed as follows. In brief, protein samples were mixed with SDS-loading buffer (50 mM Tris-HCl, pH 6.8, 100 mM dithiothreitol (DTT), 2% SDS, 0.1% bromophenol blue, and 10% glycerol) at a volume ratio of 3:1 and boiled for 5 minutes. At the same time, gels for electrophoresis including a 12% separating gel (2.5 ml of 1 M Tris, pH 8.8, 3.3 ml deionized water, 4 ml of 30% acrylamide mix, 0.1 ml of 10% SDS, 0.1 ml of 10% ammonium persulfate (APS), and 0.01 ml TEMED) and a 5% stacking gel (0.63 ml of 1 M Tris, pH 6.8, 3.4 ml deionized water, 0.83 ml of 30% acrylamide mix, 0.05 ml of 10% SDS, 0.05 ml of 10% APS, and 0.005 ml TEMED) were casted. Electrophoresis was performed at 80V for stacking and at 150V for separating. Gels were then stained with coomassie blue staining solution (0.1% coomassie R250, 10% acetic acid, and 50% methanol) for 1 hour and destained with destaining solution (10% acetic acid and 50% methanol).

Western Blotting

Western blotting was performed as follows. In brief, protein samples separated on SDS-PAGE gel were transferred to a nitrocellulose membrane at 135V. The membrane was then incubated in Tris-buffered saline with Tween-20 (referred to as TBST; 50 mM Tris, 150 mM sodium chloride, and 0.05% Tween-20) containing 5% skimmed milk to block the non-specific binding for at least 1 hour with shaking. After washed with TBST, the membrane was treated with anti-His-tag antibody (Bethyl, A190-114P) or anti-H5 hemagglutinin antibody (GeneTex, GTX41297) at a dilution factor of 1:10000 in TBST for 1 hour. After washed again with TBST, the membrane was treated with horseradish peroxidase (HRP)-conjugated anti-mouse IgG secondary antibody (GeneTex) at a dilution factor of 1:1500 in TBST for 1 hour and washed with TBST. For detection, an enhanced chemiluminescence reagent (Western Lighting Plus ECL; PerkinElmer) was added to the membrane to produce luminescence signals, which were visualized after exposure to Medical X-ray Film (Fujifilm).

Hemagglutination Assay

Two-fold serial dilution of protein samples was prepared with PBS (pH 7.4) at a starting concentration of 70 μg/ml. Afterwards, the serially diluted protein samples were added to a 96-well V-plate at 50 μl/well, and PBS containing 0.5% turkey erythrocytes was then added at 50 μl/well. The plate was allowed to sit at room temperature for 30 minutes for hemagglutination. The titer of the recombinant protein was defined as the maximum dilution at which erythrocyte precipitation was observed for the first time.

Fetuin Binding Assay

The binding solution (0.05 M carbonate buffer solution, pH 9.6) containing 100 μg/ml fetuin was added to a 96-well plate at 100 μl/well. After sitting at 4° C. for 16-18 hours, the plate was washed with PBS containing 0.05% Tween-20 (referred to as PBST). 200 μl PBS containing 1% bovine serum albumin (BSA) was then added for blocking at room temperature for 1 hour to prevent non-specific binding. Next, the 96-well plate was washed with PBST, and serially diluted protein samples (two-fold serial dilution prepared with PBS containing 1% BSA and 0.05% Tween-20 at a starting concentration of 10 μg/ml) were added to each well. The plate was incubated at room temperature for 1 hour and washed with PBST. Then, the 96-well plate was treated with 100 μl/well of anti-H5 hemagglutinin antibody (1:10000 dilution) for 1 hour, washed with PBST, and treated with 100 μl/well of HRP-conjugated anti-rabbit IgG secondary antibody (1:5000 dilution) for 1 hour at room temperature. Finally, 100 μl/well of the HRP chemiluminescence substrate, 3,3',5,5'-tetramethylbenzidine (TMB; Biolegend), was added to the 96-well plate. After color development in the dark for 15 minutes, 100 μl/well of 2 N sulfuric acid was added to stop the reaction, and the absorbance at 450 nm (O.D. 450) of each well was measured using an ELISA reader (TECAN SUNRISE™).

TLR2/1 Functional Assay

Human embryonic kidney cells HEK-293A (Invitrogen Cat # R70507) were cultured in Dulbecco's Modified Essential Medium (Invitrogen) supplemented with 5% BSA and 100 U/ml penicillin-streptomycin. To perform the TLR2/1 functional assay, HEK-293A cells were seeded in a 10 cm cell culture dish (SPL) at $6 \times 10^6$ cells/dish and incubated overnight at 37° C. under 5% $CO_2$. The cells were transfected with the pDUO-hTLR1/2 vector (InvivoGen) and the pGL4.32 [luc2p/NF-κB-RE/Hygro] vector (Promega) using the transfection reagent Turbofect (Fermentas). The culture medium was refreshed after a few hours and the cells were incubated overnight at 37° C. under 5% $CO_2$. The transfected cells were seeded in a 96-well plate at $5 \times 10^4$ cells/well, and serially diluted protein samples (from 10 ng/ml to 1 pg/ml) were added to the cells, followed by incubation at 37° C. for 5 hours. After the 96-well plate was washed with PBS, the cells were treated with cell lysis buffer (Glo-lysis buffer; Promega) for 5 minutes and then treated with 50 μl/well of luminescent substrate (neolite assay; Perkin Elmer). After 5 minutes, the Victor II microplate reader (PerkinElmer) was used to measure the relative luminescence unit (RLU) of each well at a wavelength of 560 nm.

Mice Immunization and Sample Collection

Immunization experiments were carried out with six-week-old female BALB/c mice and seven-day-old chicks. Each mouse was intranasally administered with a fixed volume of the indicated recombinant protein in PBS or PBS alone. To facilitate intranasal injection, mice were generally anesthetized with isoflurane (Panion & BF Biotech) by inhalation, and then protein samples were dropped into the nasal cavity. Each group of mice was given three immunizations at about three-week intervals. Mouse blood samples were collected two weeks after the third injection; mouse bronchoalveolar lavage fluid (BALF) as well as spleen and cervical lymph nodes (CLNs) were collected when the mice were sacrificed three weeks after the third injection. Similarly, each chick was administered with a fixed volume of recombinant protein in PBS or PBS alone by intranasal injection. Each group of chicks was injected three times at about two-week intervals. Chick blood samples were collected from the wing vein prior to injection and two weeks after the third injection. The aforementioned blood samples were heated at 56° C. for 2 hours and centrifuged at 3000 rpm for 10 minutes to separate serum from blood cells. The serum was stored at −20° C. The BALF was centrifuged at 3000 rpm for 10 minutes and the supernatant was stored at −20° C.

Determination of Antibody Levels

Enzyme-linked immunosorbent assay (ELISA) was used to determine the titers of immunoglobulin G (IgG) and immunoglobulin A (IgA) in mouse serum and BALF, and the titers of immunoglobulin Y (IgY) and IgA in chick serum. First, 100 μl/well of the binding solution containing 0.2 μg/ml of the recombinant HSHA protein was added to a 96-well plate, which sat at 4° C. for 16-18 hours before being washed with PBST and blocked with 200 μl PBS containing 1% BSA at room temperature for 1 hour. Next, the 96-well plate was washed with PBST, and each well was loaded with 100 μl of the serum or BALF that was serially diluted with PBS containing 1% BSA and 0.05% Tween-20. The plate was incubated at room temperature for 1 hour and washed with PBST. Thereafter, 100 μl/well of anti-mouse IgG antibody (1:60000 dilution), anti-mouse IgA antibody (1:50000 dilution), anti-chicken IgY antibody (1:10000 dilution), or IgA antibody (dilution 1:5000) (BETHYL) was added to the 96-well plate, which was incubated at room temperature for 1 hour and then washed with PBST. Finally, 100 μl/well of TMB was added to the 96-well plate. After color development in the dark for 15 minutes, 100 μl/well of 2 N sulfuric acid was added to stop the reaction, and the absorbance at 450 nm of each well was measured using the ELISA reader.

Preparation of H5N1 Influenza Pseudovirus

The method for preparing H5N1 influenza pseudovirus (H5N1 pseudo-type virus particle) was based on description in previous papers (Nefkens et al., 2007; Lin et al., PloS One, 2011; 6(5): e20052). HEK-293A cells were added in a 10 cm cell culture dish at $3\times10^6$ cells/dish and incubated overnight at 37° C. under 5% $CO_2$. The HEK-293A cells were transfected with the pNL-Luc-E$^-$R$^-$ plasmid (HIV backbone) with a luminescence reporter gene, the pcDNA 3.1 (+)–HA vector (A/Thailand/1(KAN-1)/2004), and the pcDNA3.1 (+)–NA vector (A/Vietnam/1203/2004) using the transfection reagent Turbofect, and the culture medium was changed after a few hours. After incubation for 48 hours at 37° C. under 5% $CO_2$, the cell culture medium was collected and stored at −20° C.

Neutralizing Antibody Assay

Madin-Darby canine kidney (MDCK) cells (provided by Dr. King-song Jeng, Academia Sinica, Taiwan) were cultured overnight in a 96-well plate at $1\times10^5$ cells/well. Thereafter, the mouse serum or BALF was serially diluted with DMEM, and 50 μl of each of the dilutions was mixed at equal volume with a fixed amount (equivalent to luminescence intensity of 40000) of the H5N1 influenza pseudovirus carrying a luminescence reporter gene for 1 hour. The mixture was added to the MDCK cells in the 96-well plate and incubated at 37° C. for 2 days. After the 96-well plate was washed with PBS, the cells were treated with cell lysis buffer (Glo-lysis buffer) for 5 minutes and then treated with 50 μl/well of luminescent substrate (neolite assay; Perkin Elmer). After 5 minutes, the Victor II microplate reader (PerkinElmer) was used to measure the relative luminescence unit (RLU) of each well at 560 nm. The decrease of luminescence values due to treatment with the serum-virus or BALF-virus mixtures, as compared to the luminescence values of control cells treated only with the pseudovirus, was used to calculate the percentage of virus neutralization and to obtain the neutralization curves. The neutralization curves and the titers of neutralizing antibodies were determined by regression analysis using the software Graph Pad Prism version 5.

Viral Hemagglutinin Inhibition (HI) Assay

Prior to the assay, 10 μl chicken serum was treated with 30 μl of a receptor destroying enzyme (RDE; Denka Seiken) at 37° C. for 18-20 hours to remove the materials causing nonspecific erythrocyte aggregation. Thereafter, the serum-enzyme mixture was heated at 56° C. for 30 minutes to eliminate the RDE activity, followed by addition of 60 μl PBS to the mixture, resulting in a final volume of 100 μl. The 100 μl serum mixture was incubated at 4° C. for 1 hour with 5 μl PBS containing 0.5% turkey erythrocytes, and a serum supernatant was collected from the mixture by centrifugation (400×g, 10 minutes, 4° C.). After the serum supernatant was two-fold serially diluted with PBS, 25 μl of each diluted solution was mixed at equal volume with 4 hemagglutination units (HA unit) of delta H5N1 virus (prepared according to Mariana Baz et al, Virus research. (2013) "H5N1 vaccines in humans") and incubated at 37° C. for 30 minutes. Then, 50 μl of 0.5% turkey erythrocytes were added, and hemagglutination was examined after the mixture was left at room temperature for 30-60 minutes.

Plaque Reduction Neutralization Test (PRNT)

Chicken serum was two-fold serially diluted in Minimum Essential Medium-a (MEM-α; Gibco), and 20 μl of each diluted solution was mixed at equal volume with 100 plaque forming units (PFUs) of delta H5N1 virus for incubation at 37° C. for 1 hour. The serum-virus mixture and 960 μl of the MEM-α medium containing 0.5 μg/ml TPCK (N-tosyl-L-phenylalanine chloromethyl ketone)-treated trypsin (Sigma) were added to 6-well plates seeded with $9.5\times10^5$ MDCK cells/well, and incubated at 37° C. for 1 hour. The cells in each well were washed with PBS and covered by 3 ml of the MEM-α medium containing 0.5 μg/ml TPCK-treated trypsin and 0.5% agar. After incubated at 37° C. for 48 hours, the cells were fixed with 4% paraformaldehyde (Sigma) for 8 hours, stained with 1% crystal violet (Sigma) in 20% formaldehyde for 8 hours, and destained with water in order for viral plaque counting. The number of viral plaques reduced by treatment with the serum-virus mixture, as compared to the number of virus plaques in the control group treated only with virus, was used to calculate the neutralization percentage and obtain the neutralization curves.

Determination of Cytokine Levels

The cells obtained by grinding tissues from mouse spleen and cervical lymph nodes were seeded in a 24-well plate at $5\times10^5$ cells/well. Thereafter, the cells were stimulated with 1 μg/ml of the peptide fragments of H5 hemagglutinin from H5N1 influenza virus (A/Vietnam/1203/2004) and cultured for 72 hours at 37° C. under 5% $CO_2$. The peptide fragments included peptide fragments 1-50 (SEQ ID NOs: 4-53) derived from the HA1 subunit and HA2 subunit of hemagglutinin. Levels of IFN-γ, IL-4, and IL-17A, secreted by T helper 1 cells (Th1 cells), T helper 2 cells (Th2 cells), and T helper 17 cells (Th17 cells), respectively, in the cell cultures were analyzed by ELISA kit (Biolegend).

Example 1

Preparation of the Antigen Fusion Protein

This example illustrates the method of preparing the antigen fusion protein that is used for preparation of the influenza mucosal vaccine composition of the present invention. The ectodomain of H5 hemagglutinin (referred to as HSHA) was used as an example of the influenza virus antigen. Accordingly, the antigen fusion protein described in all examples of the specification includes the H5 hemagglutinin ectodomain and a wild-type Type IIb heat-labile enterotoxin A subunit from *E. coli* (referred to as LTIIb-A), and is referred to as HSHA-LTIIb-A fusion protein. The LTIIb-A has the amino acid sequence of SEQ ID NO:54 or at least 90% sequence identity to SEQ ID NO:54.

To prepare the HSHA-LTIIb-A fusion protein, a DNA construct containing in sequence a gene fragment encoding the H5 hemagglutinin ectodomain and a gene encoding the LTIIb-A from the 5' end to the 3' end is prepared. The gene fragment encoding the H5 hemagglutinin ectodomain (SEQ ID NO:55) may be obtained by cloning techniques from an H5 hemagglutinin gene that was derived from the influenza A virus H5N1 strain (A/Thailand/1 (KAN-1)/2004). The gene encoding the LTIIb-A (SEQ ID NO: 56) may be obtained by cloning techniques from the chromosome of enterotoxigenic *E. coli*.

The DNA construct containing the nucleic acid encoding the HSHA-LTIIb-A fusion protein may further include a short nucleic acid positioned between the aforementioned two genes. The short nucleic acid encodes a GCN4 leucine zipper (SEQ ID NO:57) and a short peptide containing a plurality of glycine (Gly) and serine (Ser) residues, for example, a GS linker having the amino acid sequence of Gly-Gly-Ser-Gly-Gly-Gly-Ser-Gly (SEQ ID NO: 58). The GCN4 leucine zipper is used to facilitate the formation of a trimer of the HSHA-LTIIb-A fusion protein, and the GS linker is used to conjugate the H5 hemagglutinin ectodomain with the LTIIb-A.

To facilitate the subsequent protein purification, the abovementioned DNA construct may further include a DNA segment near the 5' end that encodes a polyhistidine tag (termed His-tag), so that the expressed HSHA-LTIIb-A fusion protein has a His-tag positioned at its N-terminus (amino acids 19-24). FIG. 1A shows a construction scheme illustrating the HSHA-LTIIb-A fusion protein including an N-terminal His-tag. In another embodiment, the DNA segment encoding the polyhistidine tag may be positioned near the 3' end of the DNA construct, resulting in the His-tag sitting between the GCN4 leucine zipper and the GS linker and adjacent to the C-terminus of the HSHA-LTIIb-A fusion protein. FIG. 1B shows a construction scheme illustrating the HSHA-LTIIb-A fusion protein including a His-tag in the middle. Unless specifically stated, the HSHA-LTIIb-A fusion protein described in the examples contains an N-terminal His-tag.

The HSHA-LTIIb-A fusion protein was expressed using the Bac-to-Bac baculovirus/insect cell expression system (Invitrogen). In brief, the aforementioned DNA construct was cloned into pFastbac.1 plasmid according to the manufacturer's instructions, and DH10Bac *E. coli* was transformed with this recombinant plasmid. Blue-white screening was employed to identify the *E. coli* carrying the baculovirus vector (bacmid) with the inserted DNA construct, and the bacmid was purified therefrom. The purified bacmid was transfected into Sf9 insect cells in order for cell production and release of baculovirus carrying the DNA construct in the SF900 cell culture medium (Invitrogen). The baculovirus was then added to Sf9 insect cells at a cell density of $2 \times 10^6$ cells/ml, followed by incubation at 27° C. for 48 to 72 hours in order for the cells to express and secrete the HSHA-LTIIb-A fusion protein into the SF900-II cell culture medium.

For purification of the fusion protein, the abovementioned cell culture medium was centrifuged at 10,000 rpm for 10 minutes at 4° C. to remove suspended cells, and then concentrated by a filtration device with a 10 kDa molecular weight cut-off. The concentrate was adjusted to pH 7.4 with Tris buffer (pH 8.0), filtered through a 0.45 μm filter membrane, and mixed with nickel-chelating resin (TOSOH) at 4° C. overnight for affinity binding. The HSHA-LTIIb-A fusion protein was then eluted from the resin with 30-40% buffer B. The fractions containing the purified HSHA-LTIIb-A fusion protein were concentrated in PBS using a 30 kDa centrifugal concentrator (Millipore) and stored at −20° C.

Figure 1D:
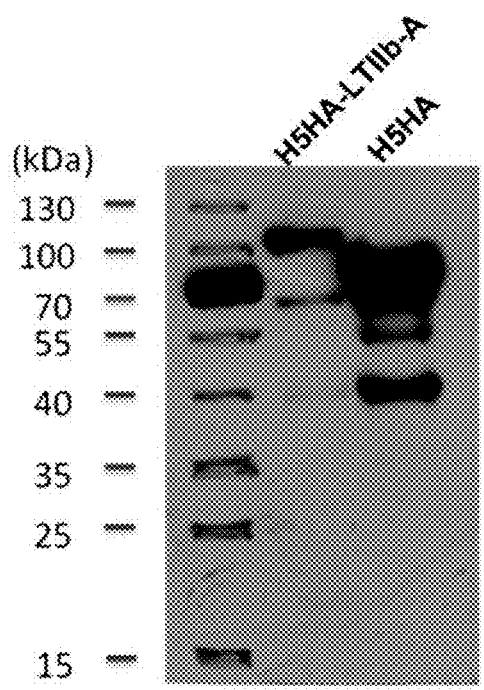
FIG. 1D shows detection of the H5HA-LTIIb-A fusion protein and the recombinant H5 HA protein by western blotting using anti-H5 hemagglutinin antibody.

The HSHA-LTIIb-A fusion protein was verified by SDS-PAGE (FIG. 1C) and Western blotting (FIG. 1D). As shown in FIG. 1C, a major protein band indicating the H5HA-LTIIb-A fusion protein was observed at about 100 kDa, close to the sum of the molecular weights of the recombinant H5HA protein (about 72 kDa) and the LTIIb-A (about 28 kDa). As shown in FIG. 1D, the H5HA-LTIIb-A fusion protein and recombinant H5HA protein was bound and detected by an anti-H5 hemagglutinin antibody, indicating that the H5HA-LTIIb-A fusion protein retained the epitopes and structural features of H5 hemagglutinin ectodomain.

These results reveal that the H5HA-LTIIb-A fusion protein can be successfully prepared according to the aforementioned method.

Figure 1E:
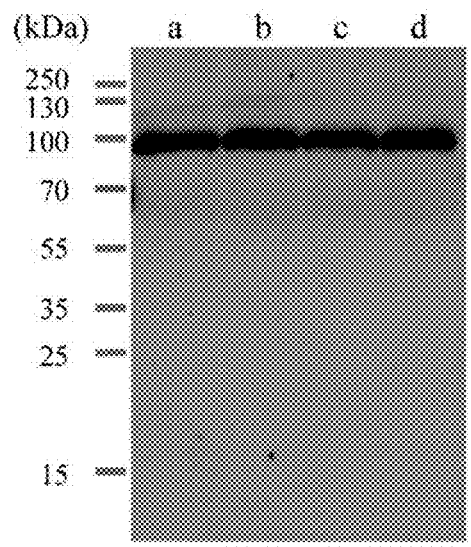
FIG. 1E shows detection of the H5HA-LTIIb-A fusion protein including N-terminal His-tag (lanes a and b) and the H5HA-LTIIb-A fusion protein including His-tag in the middle (lanes c and d) by western blotting using anti-H5 hemagglutinin antibody; the H5HA-LTIIb-A fusion protein present in lanes a and c was obtained from the cell culture medium of Sf9 insect cells expressing proteins for 48 hours; the H5HA-LTIIb-A fusion protein present in lanes b and d was obtained from the cell culture medium of Sf9 insect cells expressing proteins for 72 hours.
Figure 1F:
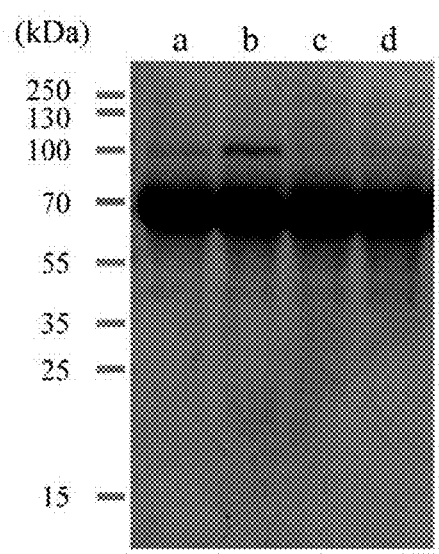
FIG. 1F shows comparison of the binding affinity between an anti-His-tag antibody and the H5HA-LTIIb-A fusion protein including N-terminal His-tag (lanes a and b) or His-tag in the middle (lanes c and d) by using western blotting; the H5HA-LTIIb-A fusion protein present in lanes a and c was obtained from the cell culture medium of Sf9 insect cells expressing proteins for 48 hours; the H5HA-LTIIb-A fusion protein present in lanes b and d was obtained from the cell culture medium of Sf9 insect cells expressing proteins for 72 hours.

To assess whether the position of His-tag affects the efficiency of purifying the H5HA-LTIIb-A fusion protein, Western blotting was employed to compare the binding affinity between an anti-His-tag antibody and the H5HA-LTIIb-A fusion protein including an N-terminal His-tag or a His-tag in the middle. According to FIG. 1E, the H5HA-LTIIb-A fusion protein including His-tag in the middle was readily detected by anti-H5 hemagglutinin antibody at about 100 kDa. However, as shown in FIG. 1F, the H5HA-LTIIb-A fusion protein including His-tag in the middle was hardly detected by anti-His-tag antibody, whereas the H5HA-LTIIb-A fusion protein including N-terminal His-tag exhibited higher binding affinity to the anti-His-tag antibody. This result shows that the H5HA-LTIIb-A fusion protein including an N-terminal His-tag improves the efficiency of protein purification with nickel-chelating resin. Therefore, the H5HA-LTIIb-A fusion proteins described in Examples 2-6 are the ones containing N-terminal His-tag. In FIG. 1F, the signal at approximately 70 kDa was resulted from proteins other than the H5HA-LTIIb-A fusion protein.

Hemagglutination assay and fetuin binding assay were performed to verify the normal structure and function of the H5 hemagglutinin ectodomain in the H5HA-LTIIb-A fusion protein. The hemagglutination assay was carried out by mixing turkey erythrocytes with serially diluted HSHA-LTIIb-A fusion protein or recombinant HSHA protein for 30 minutes. According to FIG. 2A, neither the HSHA-LTIIb-A fusion protein nor the recombinant HSHA protein at a concentration of below 0.88 μg/100 μL caused hemagglutination and erythrocyte precipitation, indicating that the HSHA-LTIIb-A fusion protein and the recombinant HSHA protein have comparable ability to bind sialic acid on erythrocytes, and thus show the same efficacy in agglutinating erythrocytes.

For the fetuin binding assay, a fixed amount of fetuin was first immobilized on a 96-well plate. Then, serially diluted HSHA-LTIIb-A fusion protein or recombinant HSHA protein was added, followed by the addition of anti-H5 hemagglutinin antibody and a chemiluminescence reagent. The change in absorbance of each well at 450 nm was detected by an ELISA reader. According to FIG. 2B, the absorbance rose to approximately 0.15 with increasing concentrations of the HSHA-LTIIb-A fusion protein and the recombinant HSHA protein, and the binding curves of these two proteins showed similar increasing trends, indicating that the two proteins have similar fetuin binding capability. Both the hemagglutination assay and the fetuin binding assay demonstrated that the conjugation of LTIIb-A to the HSHA did not significantly alter the structure and function of the HSHA region in the HSHA-LTIIb-A fusion protein.

Example 2

Activation of TLR2/1 by the H5HA-LTIIb-A Fusion Protein

TLR2/1 functional assay was performed to assess the ability of HSHA-LTIIb-A fusion protein to activate the TLR2/1 signaling pathway. First, an expression vector of human TLR2/1 and an NF-κB luciferase reporter vector were co-transfected into HEK-293A cells so that the TLR2/1 was expressed on the surface of HEK-293A cells. Next, serial dilutions of the HSHA-LTIIb-A fusion protein, the recombinant H5HA protein, the recombinant LTIIb-B5 protein, or a combination of the H5HA-LTIIb-A fusion protein and the recombinant LTIIb-B5 protein were added to the cells. Since the TLR2/1 activated by the abovementioned protein samples would induce the binding between the transcription factor NF-κB and the NF-κB response element in the NF-κB luciferase reporter vector and trigger the expression of the downstream luciferase gene, TLR2/1 activation could be assessed by detection of the luminescence intensity of HEK-293A cell lysates treated with a luminescent substrate.

Figure 3:
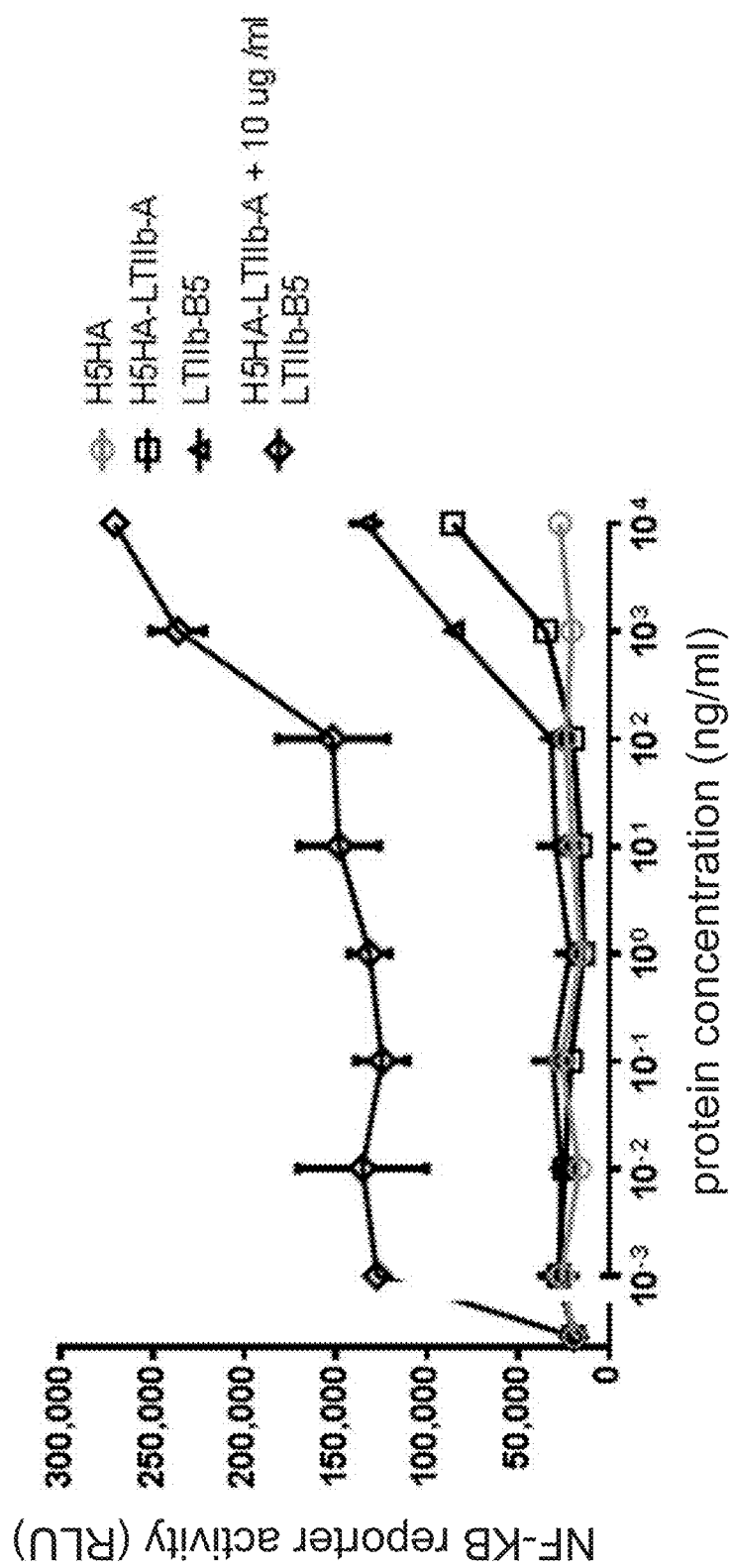
FIG. 3 shows detection of the TLR2/1 and NF-κB activation by various protein samples using TLR2/1 functional assay; the various protein samples include the recombinant H5HA protein, the H5HA-LTIIb-A fusion protein, a recombinant protein of E. coli type IIb heat-labile enterotoxin B subunit (LTIIb-B5), and the combination of the H5HA-LTIIb-A fusion protein and $10^4$ ng/ml of the recombinant LTIIb-B5 protein (denoted as H5HA-LTIIb-A+10 μg/ml LTIIb-B5)
Figure 4A:
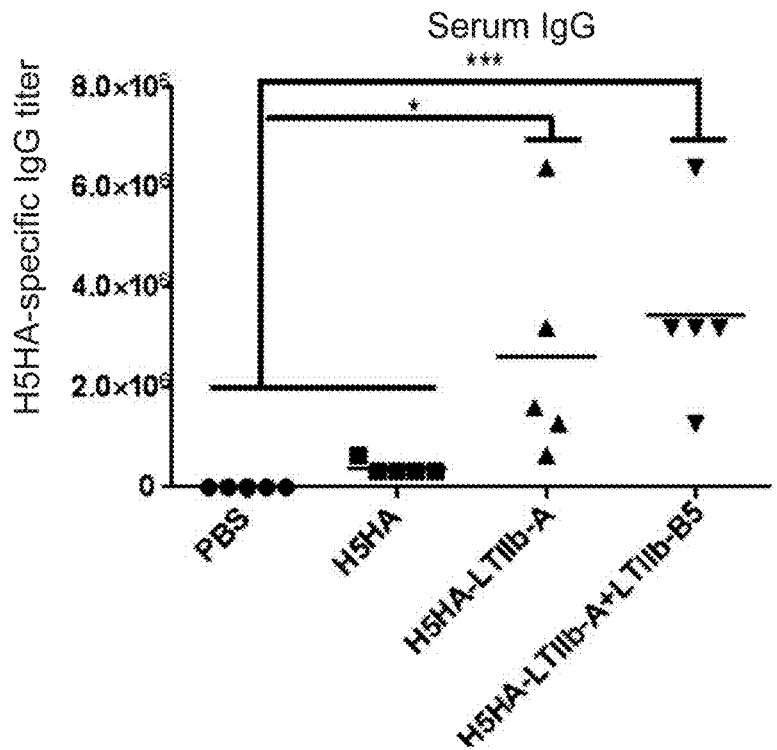
FIG. 4A and FIG. 4B respectively show titers of the anti-recombinant H5HA protein immunoglobulin G (IgG) and immunoglobulin A (IgA) in serum of BALB/c mice immunized with phosphate buffered saline (PBS), the recombinant H5HA protein, the H5HA-LTIIb-A fusion protein, or the combination of the H5HA-LTIIb-A fusion protein and the recombinant LTIIb-B5 protein (denoted as H5HA-LTIIb-A+LTIIb-B5)
Figure 4B:
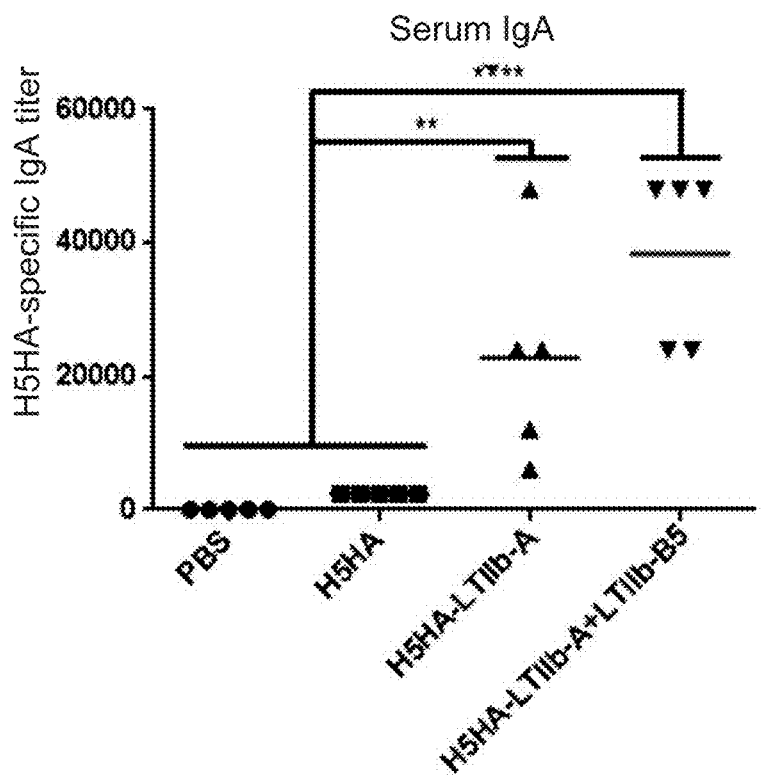
Figure 4C:
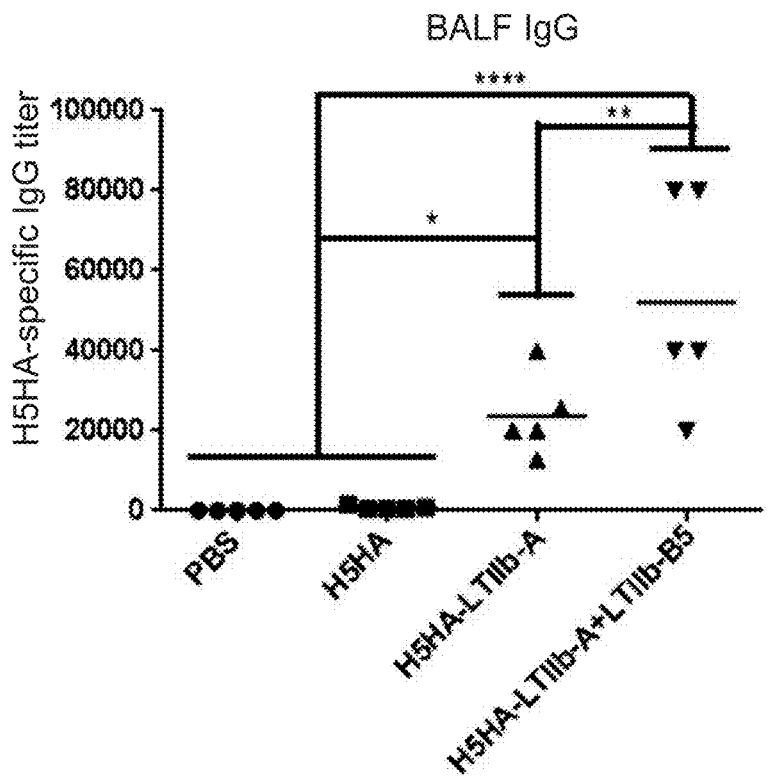
FIG. 4C and FIG. 4D respectively show titers of the anti-recombinant H5HA protein IgG and IgA in bronchoalveolar lavage fluid (BALF) of BALB/c mice immunized with PBS, the recombinant H5HA protein, the H5HA-LTIIb-A fusion protein, or the combination of the H5HA-LTIIb-A fusion protein and the recombinant LTIIb-B5 protein.
Figure 4D:
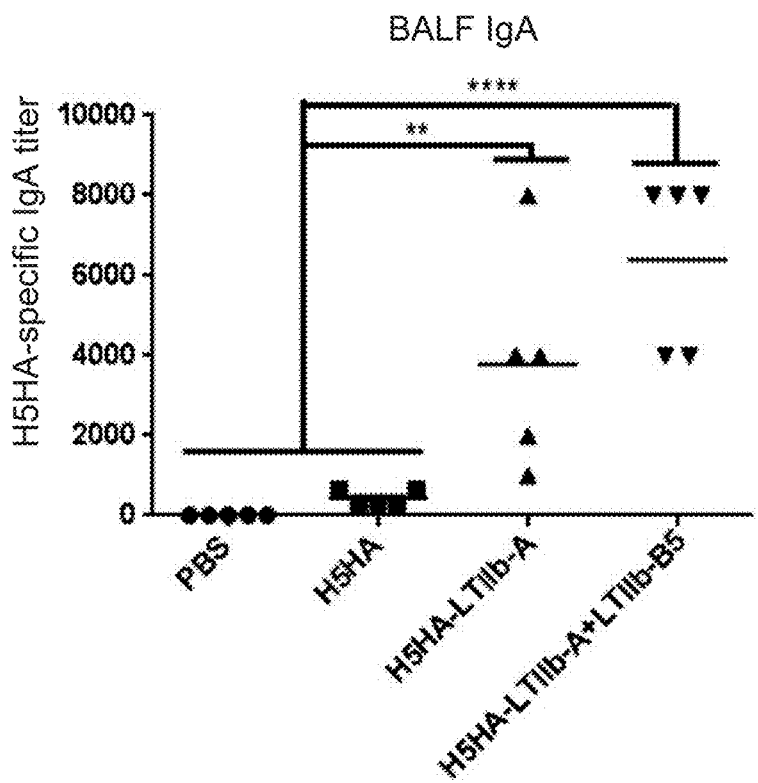

FIG. 3 shows the results obtained in the aforementioned assay. Treatment with $10^4$ ng/ml of the recombinant H5HA protein led to a luminescence intensity value close to the background value for untreated cells; the luminescence intensity was approximately 6-fold of the background value after treatment with $10^4$ ng/ml of the recombinant LTIIb-B5 protein; and the luminescence intensity was approximately 4-fold of the background value after treatment with $10^4$ ng/ml of the H5HA-LTIIb-A fusion protein. The luminescence intensity values were found similar in cells treated with both the H5HA-LTIIb-A fusion protein at low concentrations ($10^{-3}$ to $10^2$ ng/ml) and $10^4$ ng/ml of the recombinant LTIIb-B5 protein and those treated only with $10^4$ ng/ml of the recombinant LTIIb-B5 protein. However, the luminescence intensity was higher in cells treated with both $10^4$ ng/ml of the H5HA-LTIIb-A fusion protein and $10^4$ ng/ml of the recombinant LTIIb-B5 protein, compared to that of cells treated solely with $10^4$ ng/ml of the H5HA-LTIIb-A fusion protein alone or $10^4$ ng/ml of the recombinant LTIIb-B5 protein. These results show that the antigen fusion protein disclosed by the present invention is able to activate TLR2/1 and contributes to the induction of innate immunity in a subject. Moreover, according to this example, the combined use of the H5HA-LTIIb-A fusion protein and the recombinant LTIIb-B5 protein produces the most significant TLR2/1 activating effect. This result also suggests that similar effects could be achieved by a fusion protein that is formed from conjugating the HSHA-LTIIb-A fusion protein with the LTIIb-B5 protein.

Example 3

Systemic and Mucosal Immunogenic Effects of the H5HA-LTIIb-A Fusion Protein in Mice To examine whether the HSHA-LTIIb-A fusion protein effectively elicits the systemic and mucosal immune responses in mammals against influenza virus, BALB/c mice (5 mice per group) were administered, via intranasal injection, with three doses of the HSHA-LTIIb-A fusion protein (10 μg), the recombinant HSHA protein (10 μg), the HSHA-LTIIb-A fusion protein (10 μg) in combination with the recombinant LTIIb-B5 protein (5 μg), or PBS (as negative control), followed by determination of the HSHA-specific IgG and IgA levels in mouse serum and BALF using enzyme-linked immunosorbent assay (ELISA). The time interval between each of the immunizations was approximately three weeks. Mouse blood samples were collected two weeks after the third injection. Mouse bronchoalveolar lavage fluids (BALF) were collected when the mice were sacrificed three weeks after the third injection. The titer of anti-recombinant HSHA protein IgG or IgA in mouse serum or BALF was the fold of dilution for achieving four times the absorbance of the negative control.

FIG. 4A and FIG. 4B respectively show titers of the anti-recombinant HSHA protein IgG and IgA in mouse serum. Both data points and the average for each treatment are presented in the figures, where * indicates $p<0.05$,  indicates $p<0.01$, * indicates $p<0.001$, and ** indicates $p<0.0001$. According to FIG. 4A, IgG was not detected in serum after PBS immunization, and injection with the recombinant HSHA protein elicited only small amounts of IgG. In contrast, the HSHA-LTIIb-A fusion protein in combination with the recombinant LTIIb-B5 protein induced the highest production of IgG, followed by the H5HA-LTIIb-A fusion protein. According to FIG. 4**B, IgA was not detected in serum after PBS immunization, and injection with the recombinant H5HA protein elicited only small amounts of IgA. In contrast, the H5HA-LTIIb-A fusion protein in combination with the recombinant LTIIb-B5 protein induced the highest production of IgA, followed by the H5HA-LTIIb-A fusion protein. The results show that the antigen fusion protein of the present invention elicits significantly more antigen-specific IgG and IgA in serum.

FIG. 4C and FIG. 4D respectively show titers of the anti-recombinant H5HA protein IgG and IgA in mouse BALF. Both data points and the average for each treatment are presented in the figures, where * indicates $p<0.05$,  indicates $p<0.01$, and  indicates $p<0.0001$. According to FIG. 4C, IgG was not detected in BALF after immunization with PBS or the recombinant H5HA protein. However, the H5HA-LTIIb-A fusion protein in combination with the recombinant LTIIb-B5 protein or the H5HA-LTIIb-A fusion protein alone induced significantly higher amounts of IgG, and the former treatment resulted in significantly higher IgG levels. According to FIG. 4**D, when compared to the group immunized with PBS or the recombinant H5HA protein, the combination of the H5HA-LTIIb-A fusion protein and the recombinant LTIIb-B5 protein or the H5HA-LTIIb-A fusion protein alone elicited significantly higher amounts of IgA, and the former treatment resulted in higher IgA levels. These results show that administration of the antigen fusion protein of the present invention to mammals significantly increases the levels of IgG and IgA having specificity for the antigen, in particular, the IgA levels in BALF. Therefore, the antigen fusion protein of the present invention enhances the systemic and mucosal immune responses in mammals against the influenza virus antigen. Moreover, according to this example, the combined use of the H5HA-LTIIb-A fusion protein and the recombinant LTIIb-B5 protein further increases the antigen-specific antibodies in a subject.

Example 4

Induction of Influenza Virus Neutralizing Antibodies in Mice by the H5HA-LTIIb-A Fusion Protein This example determines the titers of neutralizing antibodies against H5N1 influenza pseudovirus in serum and BALF of the mice immunized differently according to the method described in Example 3. Briefly, serial dilutions of the serum or BALF were incubated with the H5N1 influenza pseudovirus carrying a luminescence reporter gene at 37° C. for 1 hour. Next, the neutralizing antibody assay was performed by adding the various mixtures of the pseudovirus and the serum or BALF to a 96-well plate seeded with MDCK cells in order to obtain neutralization curves. The titer of neutralizing antibodies is defined as the fold of dilution of the serum or BALF that is required to reduce virus infection by 50%.

FIG. 5A and FIG. 5B show the neutralization curves of H5N1 influenza pseudovirus neutralizing antibodies in mouse serum and BALF, respectively. According to FIG. 5A, no more than 50% of the pseudovirus was neutralized by antiserum, at any concentration, to the recombinant HSHA protein or PBS. However, 90% of the pseudovirus was neutralized by the highest concentration of antiserum to the HSHA-LTIIb-A fusion protein, and the pseudovirus was neutralized completely by the highest concentration of antiserum to the HSHA-LTIIb-A fusion protein in combination with the recombinant LTIIb-B5 protein. According to FIG. 5B, no more than 60% of the pseudovirus was neutralized by BALF at any concentration after immunization with PBS or the recombinant HSHA protein. In contrast, 90% of the pseudovirus was neutralized by the highest concentration of BALF obtained after immunization with the HSHA-LTIIb-A fusion protein, and the pseudovirus was totally neutralized by the highest concentration of BALF obtained after immunization with the HSHA-LTIIb-A fusion protein in combination with the recombinant LTIIb-B5 protein.

Figures 5C, 5D:
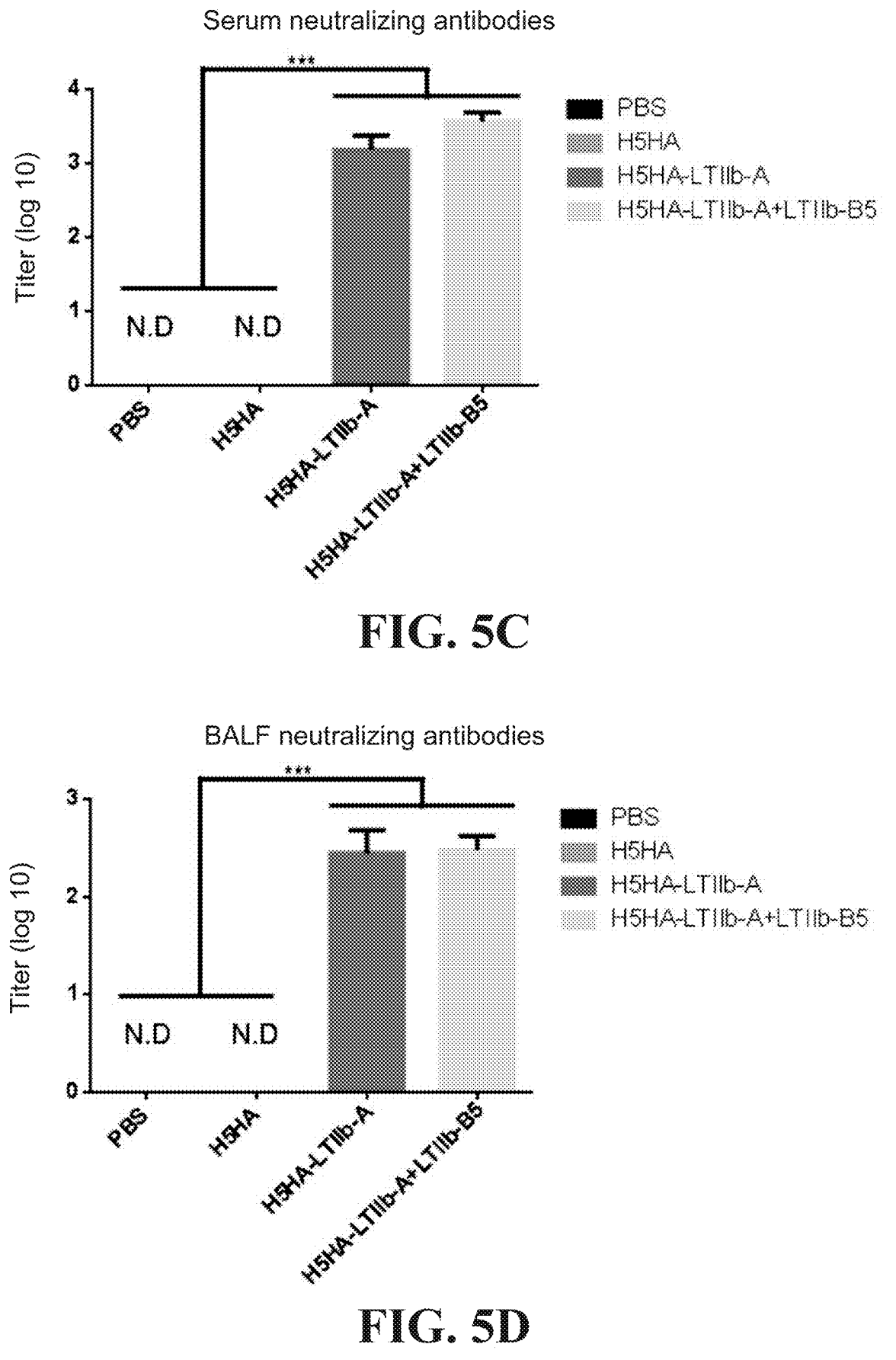

FIG. 5C and FIG. 5D show titers of neutralizing antibodies determined based on the data shown in FIG. 5A and FIG. 5B, respectively, where *** indicates p<0.001 and N.D indicates "not detected". According to FIG. 5C, the titers of serum neutralizing antibodies after immunization with PBS or the recombinant HSHA protein were approximately 155 and 34, respectively. The titer of serum neutralizing antibodies elicited by the HSHA-LTIIb-A fusion protein was approximately 1541, and the titer of serum neutralizing antibodies elicited by the combination of the HSHA-LTIIb-A fusion protein and the recombinant LTIIb-B5 protein was approximately 3662. According to FIG. 5D, the titers of neutralizing antibodies in BALF after immunization with PBS or the recombinant HSHA protein were approximately 57 and 32, respectively. The titer of BALF neutralizing antibodies elicited by the HSHA-LTIIb-A fusion protein was approximately 282, which was the same titer observed in the group co-immunized with the HSHA-LTIIb-A fusion protein and the recombinant LTIIb-B5 protein. The results show that the antigen fusion protein of the present invention induces significantly more neutralizing antibodies in mammals, including neutralizing antibodies in BALF, and thus improves inhibition of influenza viral infection of cells. Moreover, according to this example, the combined use of the HSHA-LTIIb-A fusion protein and the recombinant LTIIb-B5 protein further increases the production of influenza virus neutralizing antibodies in a subject.

Example 5

Induction of the T-Cell Related Immune Response in Mice by the H5HA-LTIIb-A Fusion Protein T cell-related immune responses were evaluated for mice immunized differently according to the method described in Example 3. After the mice were sacrificed, spleens and cervical lymph nodes (CLNs) were collected and ground, and a fixed amount of the cells obtained therefrom were cultured in a 24-well plate. A mixture of H5 hemagglutinin peptides (SEQ ID NOs:4-53) were used to stimulates the T cells in spleen and CLNs, and the levels of IFN-γ, IL-4, and IL-17A respectively secreted by Th1, Th2, and Th17 cells were measured.

Figure 6A:
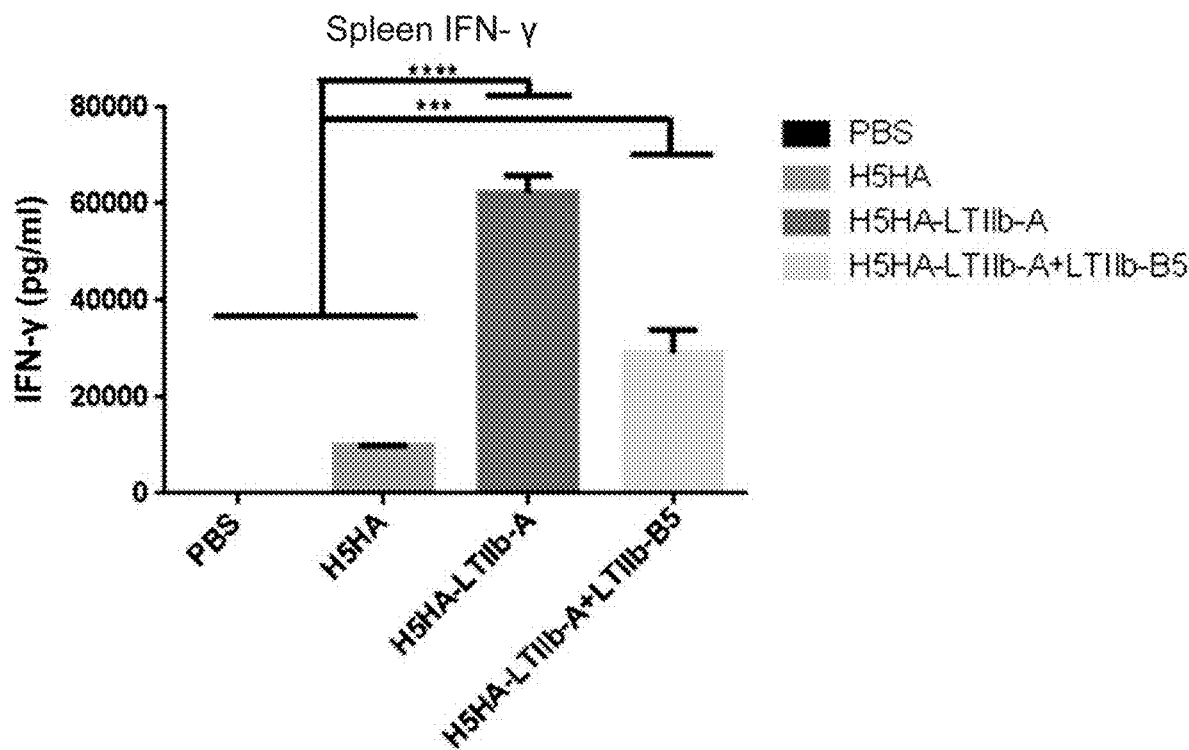
FIG. 6A and FIG. 6B respectively show the levels of IFN-γ secreted by the stimulated T cells from spleen and cervical lymph nodes (CLNs) of BALB/c mice immunized with PBS, the recombinant H5HA protein, the H5HA-LTIIb-A fusion protein, or the combination of the H5HA-LTIIb-A fusion protein and the recombinant LTIIb-B5 protein.
Figure 6B:
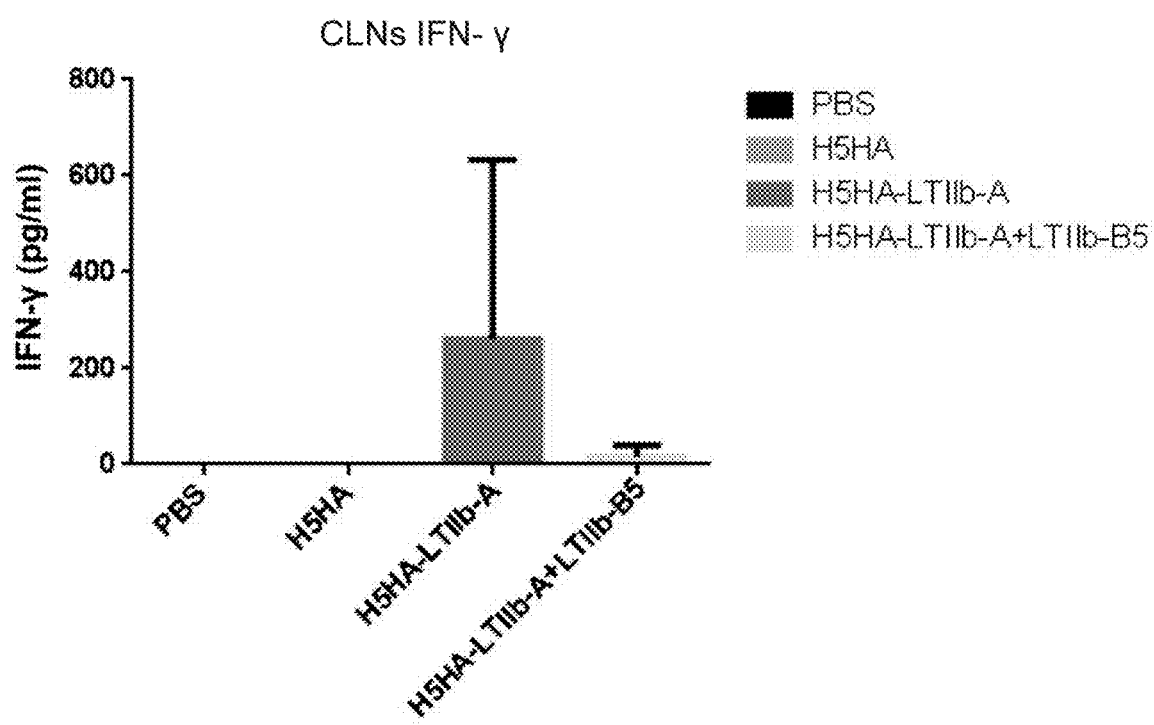

FIG. 6A and FIG. 6B show the levels of IFN-γ secreted by the stimulated T cells of mouse spleen and CLNs, respectively, where ** indicates p<0.0001 and * indicates p<0.001. According to FIG. 6A, IFN-γ was not secreted by the spleen cells of PBS-immunized mice, and only trace amounts of IFN-γ were secreted by the spleen cells of mice immunized with the recombinant H5HA protein. However, in comparison to these trace amounts, a threefold increase in IFN-γ secretion was observed in cells from the mice immunized with both the H5HA-LTIIb-A fusion protein and the recombinant LTIIb-B5 protein, and the secretion of IFN-γ was enhanced by six times in cells from the mice immunized with the H5HA-LTIIb-A fusion protein. According to FIG. 6B, IFN-γ was not secreted by the CLN cells of mice immunized with PBS or the recombinant H5HA protein. A small amount of IFN-γ was secreted by the CLN cells of mice immunized with both the H5HA-LTIIb-A fusion protein and the recombinant LTIIb-B5 protein, while the highest secretion of IFN-γ was observed in cells from the mice immunized with the H5HA-LTIIb-A fusion protein.

FIG. 6C and FIG. 6D show the levels of IL-4 secreted by the stimulated T cells of mouse spleen and CLNs, respectively. According to FIG. 6C, IL-4 was not secreted by the spleen cells of PBS-immunized mice, and only trace amounts of IL-4 were secreted by the spleen cells of mice immunized with the recombinant H5HA protein. Comparatively, the highest secretion of IL-4 was observed in cells from the mice co-immunized with the H5HA-LTIIb-A fusion protein and the recombinant LTIIb-B5 protein, and the second-high IL-4 secretion was achieved by the cells of mice immunized with the H5HA-LTIIb-A fusion protein. According to FIG. 6D, no IL-4 secretion was observed in the CLN cells of mice immunized with PBS, recombinant HSHA protein, or the combination of the HSHA-LTIIb-A fusion protein and the recombinant LTIIb-B5 protein, whereas 0.5 pg/ml of IL-4 was produced by the cells of mice immunized with the HSHA-LTIIb-A fusion protein.

Figure 6E:
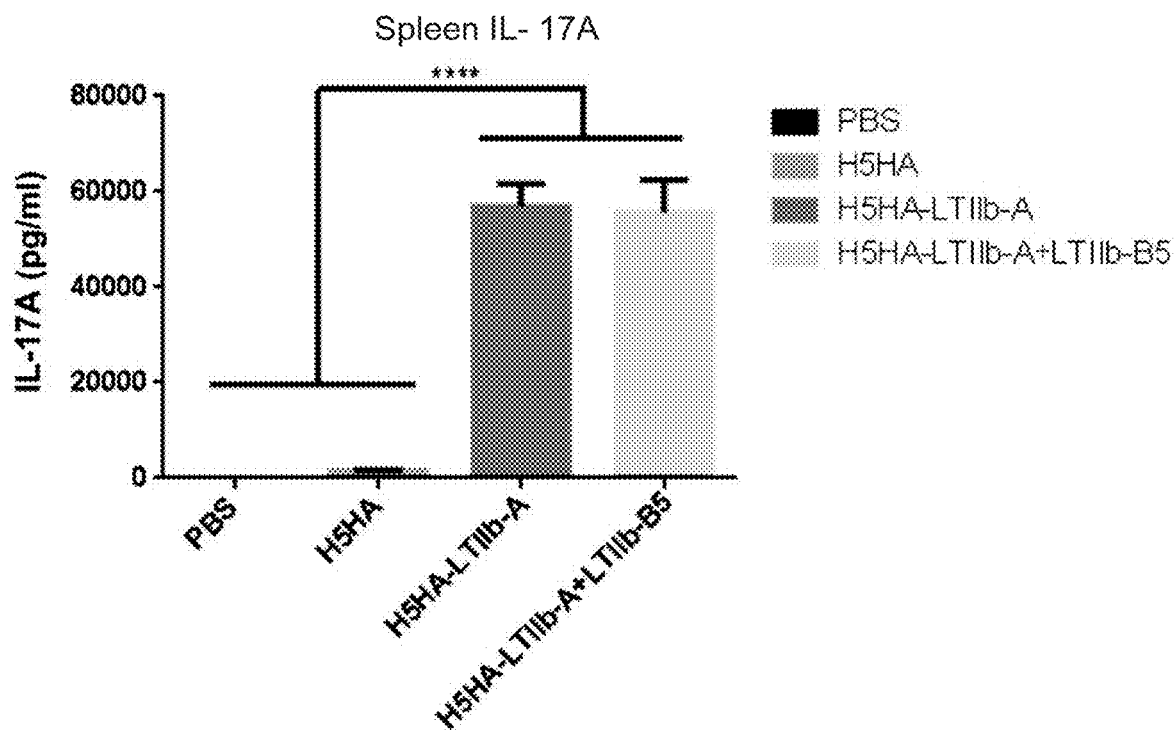
FIG. 6E and FIG. 6F respectively show the levels of IL-17A secreted by the stimulated T cells from spleen and CLNs of BALB/c mice immunized with PBS, the recombinant H5HA protein, the H5HA-LTIIb-A fusion protein, or the combination of the H5HA-LTIIb-A fusion protein and the recombinant LTIIb-B5 protein.
Figure 6F:
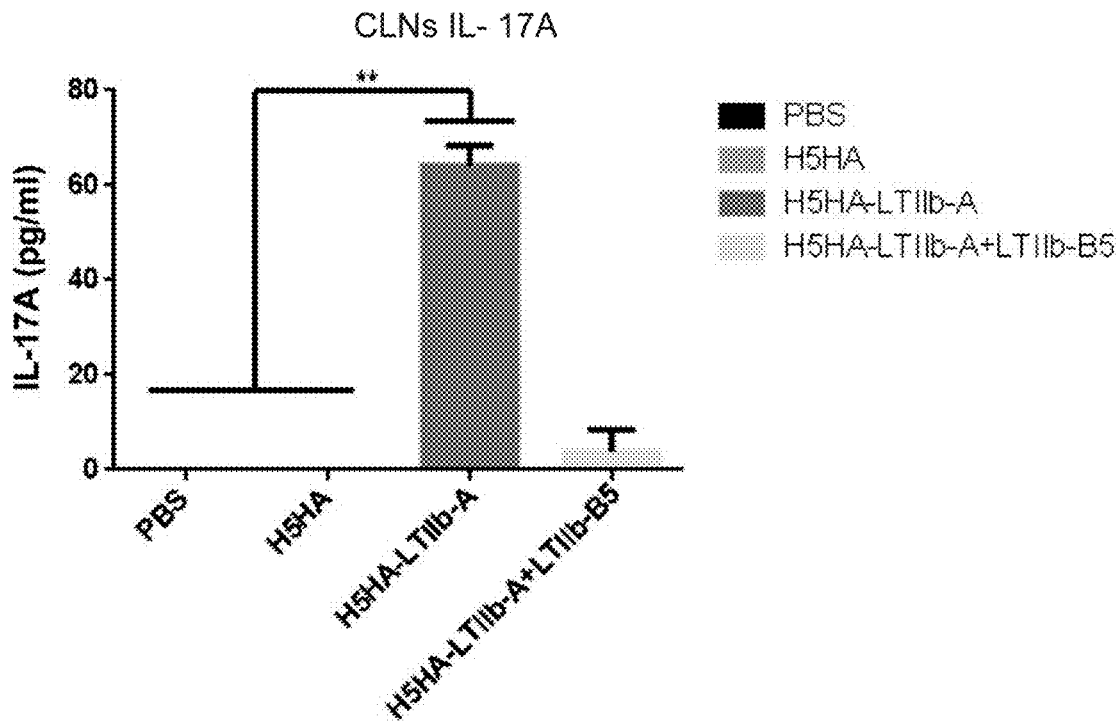

FIG. 6E and FIG. 6F show the levels of IL-17A secreted by the stimulated T cells of mouse spleen and CLNs, respectively, where ** indicates p<0.0001 and  indicates p<0.01. According to FIG. 6E, IL-17A was not secreted by the spleen cells of PBS-immunized mice, and only trace amounts of IL-17A were secreted by the spleen cells of mice immunized with the recombinant HSHA protein. In contrast, IL-17A secretion was significantly enhanced in cells from the mice immunized with the HSHA-LTIIb-A fusion protein alone or co-immunized with the HSHA-LTIIb-A fusion protein and the recombinant LTIIb-B5 protein. According to FIG. 6F, IL-17A was not secreted by the CLN cells of mice immunized with PBS or the HSHA recombinant protein. A small amount of IL-17A was secreted by the CLN cells of mice immunized with both the HSHA-LTIIb-A fusion protein and the recombinant LTIIb-B5 protein, while a significant increase in IL-17A secretion was observed in cells from the mice immunized with the HSHA-LTIIb-A fusion protein. These results show that the antigen fusion protein of the present invention can induce T cell-related immune responses, particularly IFN-γ production, in a subject. Moreover, according to this example, immunization with the HSHA-LTIIb-A fusion protein stimulates the highest secretion of IFN-γ, IL-4, and IL-17A, but the production of these cytokines is interfered with by the combined use of the recombinant LTIIb-B5 protein with the HSHA-LTIIb-A fusion protein.

Example 6

Protection Against H5N1 Influenza Virus Infection in Mice Immunized with the H5HA-LTIIb-A Fusion Protein To verify that the vaccine composition containing the HSHA-LTIIb-A fusion protein is effective in protecting subjects from H5N1 influenza virus infection, BALB/c mice (5 mice per group) were first administered, via intranasal injection, with three doses of the HSHA-LTIIb-A fusion protein (10 µg, 5 µg, or 2.5 µg), the recombinant HSHA protein (10 µg, 5 µg, or 2.5 µg), the HSHA-LTIIb-A fusion protein (10 µg, 5 µg, or 2.5 Mg) in combination with the recombinant LTIIb-B5 protein (5 µg), or PBS, where the time interval between each of the immunizations was approximately three weeks. Two weeks after the third immunization, each of the mice was injected with a 20-fold lethal dose of H5N1 virus (NIBRG-14; provided by Dr. Jan Jia-Tsrong at Genomics Research Center, Academia Sinica, Taiwan). The survival and body weight of the mice were recorded every day for 14 days for determination of survival rates and relative body weight.

Figure 7A:
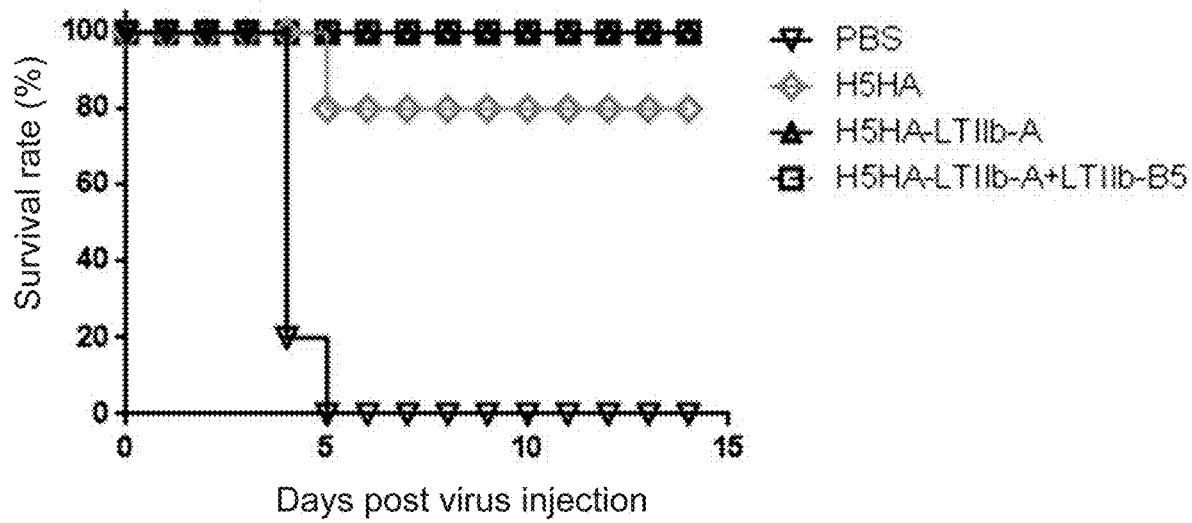
FIG. 7A shows the survival curves of BALB/c mice immunized with PBS, 10 μg of the recombinant H5HA protein, 10 μg of the H5HA-LTIIb-A fusion protein, or the combination of 10 μg of the H5HA-LTIIb-A fusion protein and 5 μg of the recombinant LTIIb-B5 protein, and then injected with H5N1 virus.

FIGS. 7A, 7C, and 7E show the survival curves of mice immunized with different doses of the indicated immunogens and then injected with H5N1 virus, where * indicates $p<0.05$. In the experiments using 10 μg or 5 μg of immunogens (as shown in FIG. 7A and FIG. 7C, respectively), all of the PBS-immunized mice died 5 or 6 days after viral injection, whereas a survival rate of greater than 80% at day 14 post virus infection was observed in mice immunized with either one of the recombinant HSHA protein, the HSHA-LTIIb-A fusion protein, or the combination of the HSHA-LTIIb-A fusion protein and the recombinant LTIIb-B5 protein. No significant difference in the survival rates was found between these three groups. However, when the amount of immunogen for administration was reduced to 2.5 μg (FIG. 7E), there was a significant difference in the survival rates between the mice immunized with the recombinant HSHA protein or the HSHA-LTIIb-A fusion protein. The survival rate of mice immunized with the recombinant HSHA protein was 25% at day 6 after virus injection; the survival rate of mice immunized with the HSHA-LTIIb-A fusion protein was 100% at day 14 after virus injection; and the survival rate of mice co-immunized with the HSHA-LTIIb-A fusion protein and the recombinant LTIIb-B5 protein was 80% at day 13 after virus injection. The results indicate that administration of the antigen fusion protein of the present invention provides subjects with the best protection against influenza virus infection compared to the administration of simply influenza virus antigens.

Figure 7B:
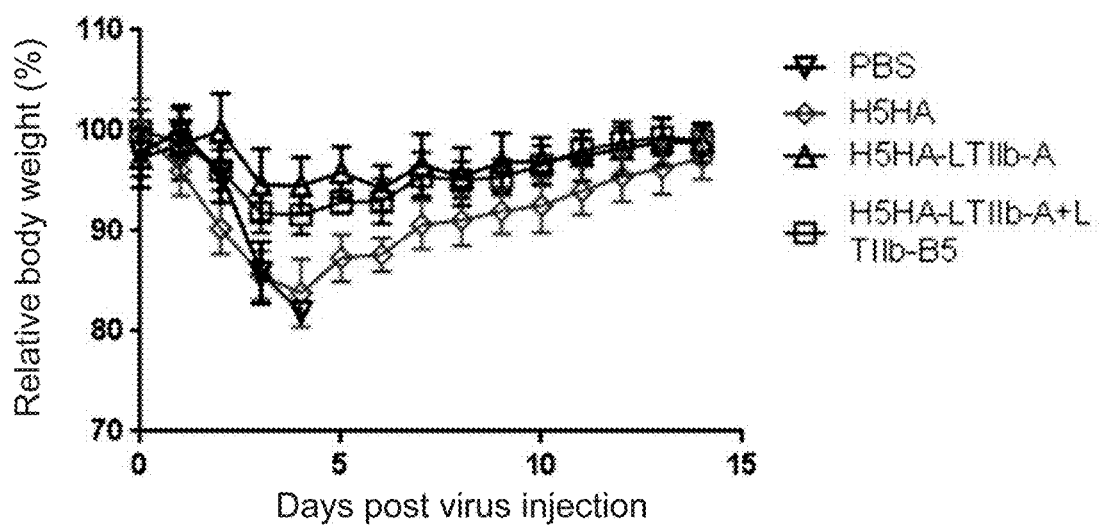
FIG. 7B shows the relative body weight of BALB/c mice immunized with PBS, 10 μg of the recombinant H5HA protein, 10 μg of the H5HA-LTIIb-A fusion protein, or the combination of 10 μg of the H5HA-LTIIb-A fusion protein and 5 μg of the recombinant LTIIb-B5 protein, and then injected with H5N1 virus.
Figures 7C, 7D:
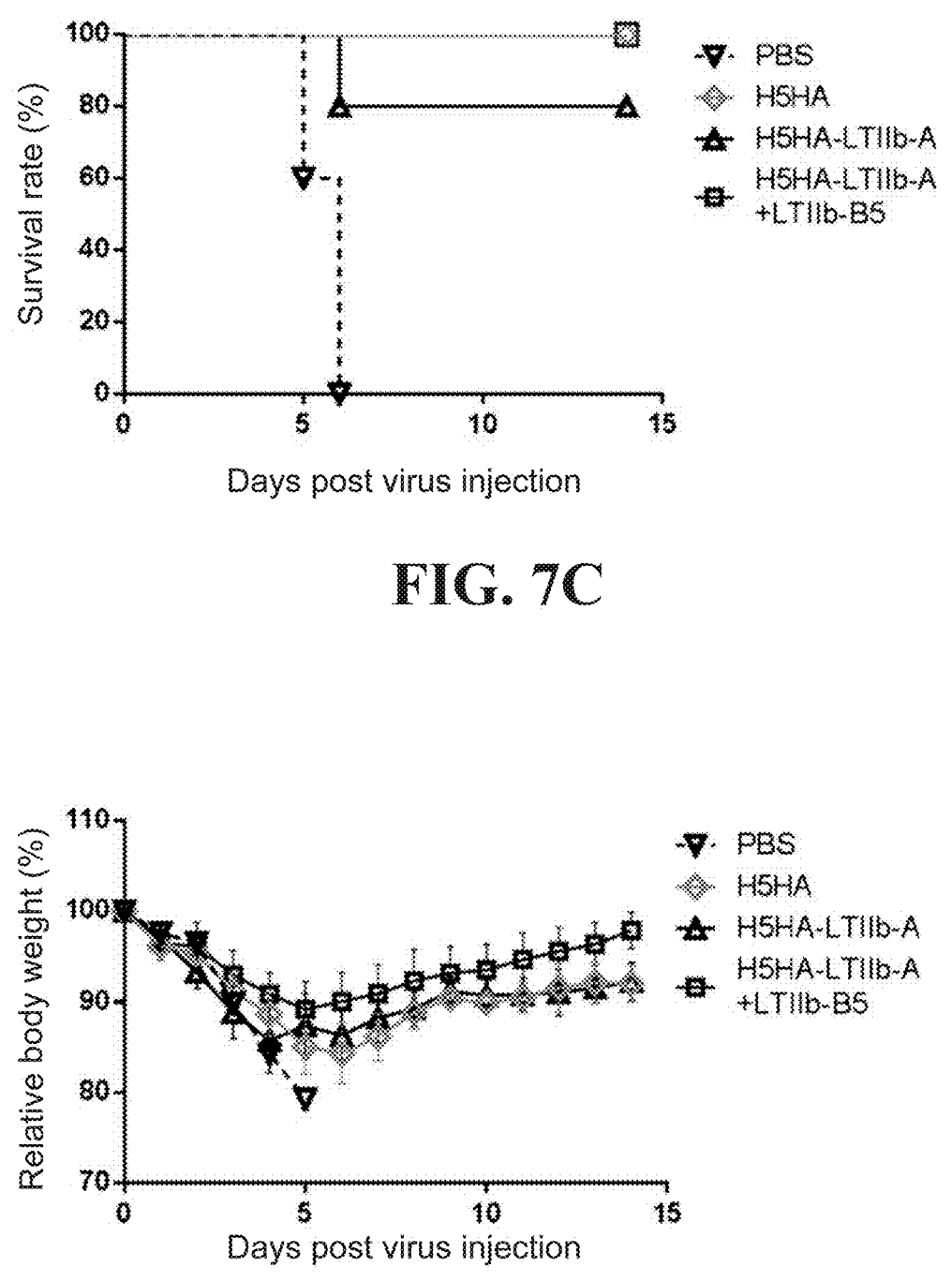
Figures 7E, 7F:
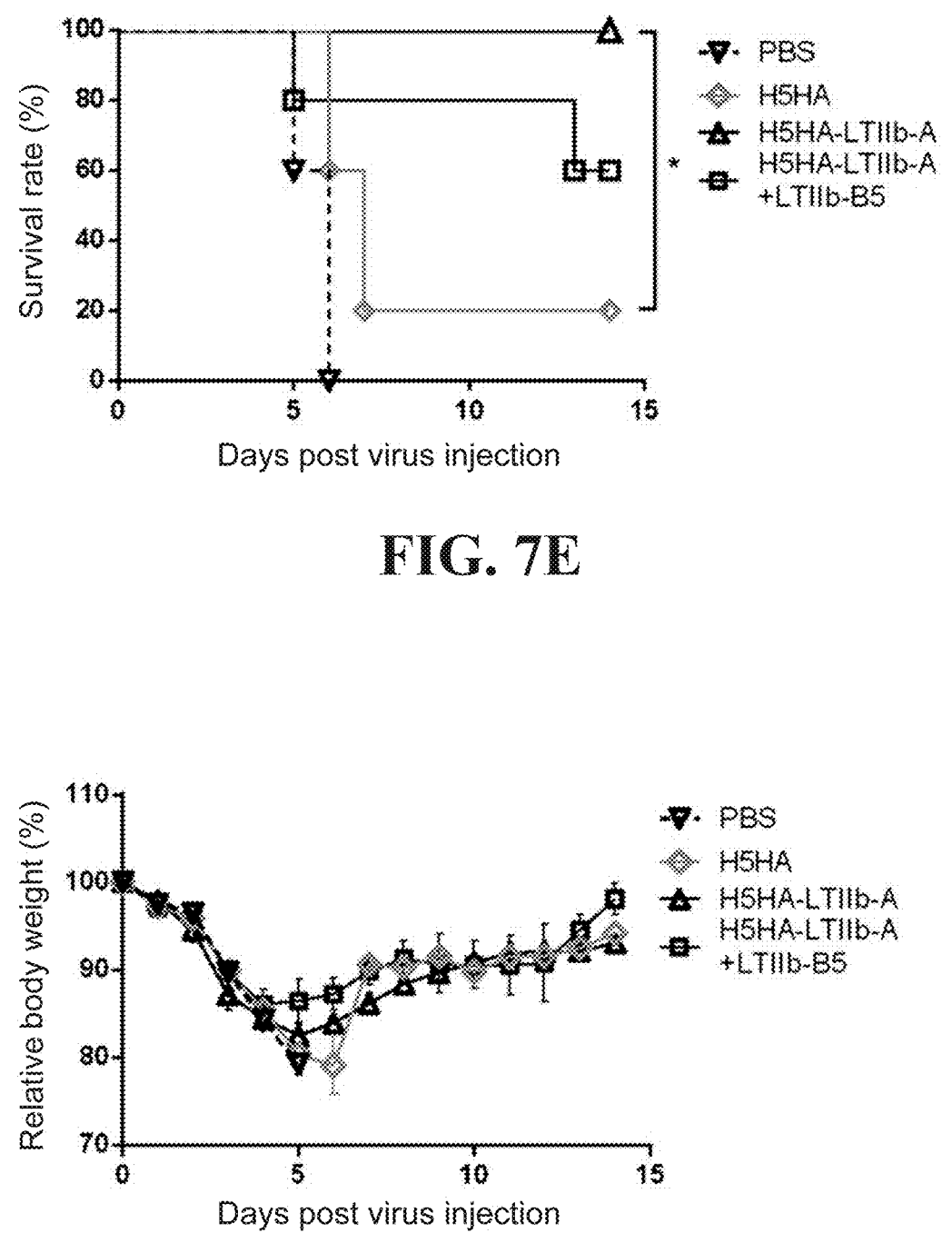

FIGS. 7B, 7D, and 7F show the relative body weight of mice immunized with different doses of the indicated immunogens and then injected with H5N1 virus, where the body weight of each mouse at day 0 was set as 100% and the body weight at the follow-up time points was normalized to that at day 0. In the experiments using 10 μg of immunogens (FIG. 7B), the relative body weight of mice immunized with the recombinant HSHA protein declined to 80% at day 4 after virus injection but returned to 95% at day 14; the relative body weight of mice immunized with the HSHA-LTIIb-A fusion protein remained not less than 95% during the 14 days after virus injection and recovered to the initial value over time; the relative body weight of mice co-immunized with the HSHA-LTIIb-A fusion protein and the recombinant LTIIb-B5 protein decreased to 90% at day 4 and then recovered to the initial value over time. In the experiments using 5 μg of immunogen (FIG. 7D), the relative body weight of mice immunized with the recombinant HSHA protein declined to 84% at day 6 after virus injection but returned to 92% at day 14; the relative body weight of mice immunized with the HSHA-LTIIb-A fusion protein dropped to 85% at day 4 after virus injection but returned to 92% at day 14; the relative body weight of mice co-immunized with the HSHA-LTIIb-A fusion protein and the recombinant LTIIb-B5 protein decreased to 89% at day 5 after virus injection but rebounded to 97% at day 14. In the experiments using 2.5 μg of immunogen test (FIG. 7F), the relative body weight of mice immunized with the recombinant HSHA protein declined to 79% at day 6 after virus injection but returned to 94% at day 14; the relative body weight of mice immunized with the HSHA-LTIIb-A fusion protein dropped to 82% at day 5 after virus injection but increased to 93% at day 14; the relative body weight of mice co-immunized with the HSHA-LTIIb-A fusion protein and the recombinant LTIIb-B5 protein decreased to fell to 86% at day 5 after virus injection but rebounded to 98% at day 14. These results show that administration of the antigen fusion protein of the present invention has less effect on body weight compared with the influenza virus antigen itself, and therefore is considered certainly safe.

Example 7

Systemic Immunogenic Effects of the H5HA-LTIIb-A Fusion Protein in Chicken

To examine whether the HSHA-LTIIb-A fusion protein effectively elicits the systemic immune response in birds against influenza virus, chicks (3 per group) were administered, via intranasal injection, with three doses of the HSHA-LTIIb-A fusion protein (10 μg), the recombinant HSHA protein (10 μg), the HSHA-LTIIb-A fusion protein (10 μg) in combination with the recombinant LTIIb-B5 protein (5 μg), or PBS (as negative control), followed by determination of the HSHA-specific IgY and IgA levels in chick serum using ELISA. The time interval between each of the immunizations was approximately two weeks. Chicken blood samples were collected before injection and two weeks after the third injection.

Figure 8A:
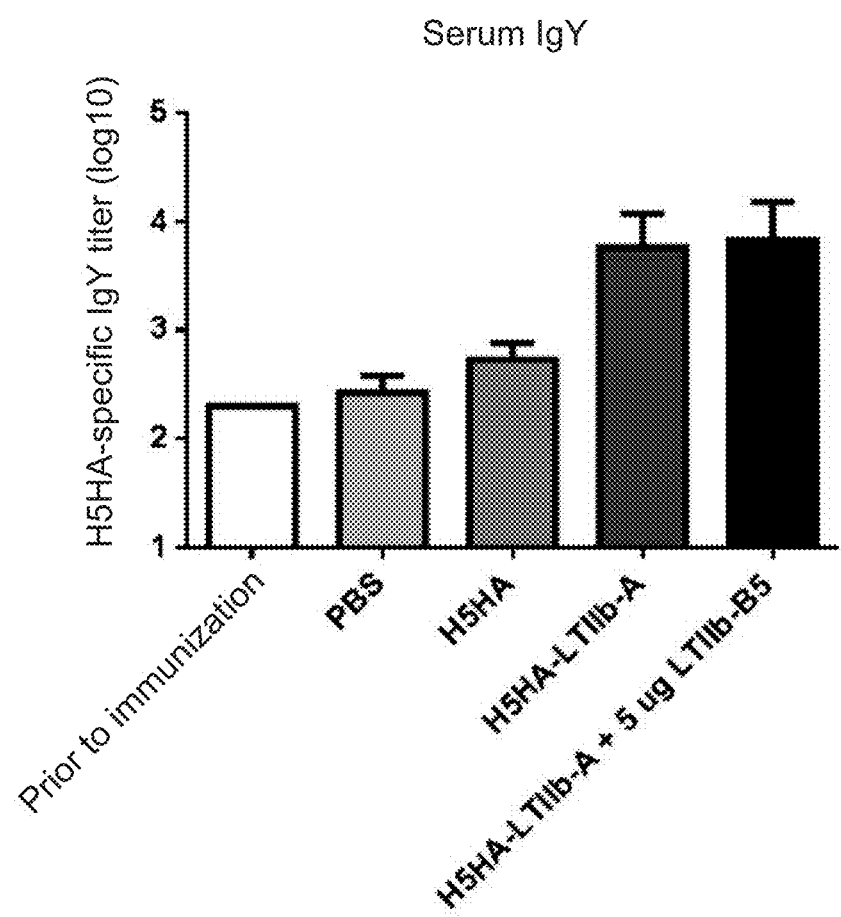
FIG. 8A and FIG. 8B respectively show titers of the anti-recombinant HSHA protein immunoglobulin Y (IgY) and IgA in serum of chick immunized with PBS, the recombinant HSHA protein, the HSHA-LTIIb-A fusion protein, or the combination of the HSHA-LTIIb-A fusion protein and the recombinant LTIIb-B5 protein.
Figure 8B:
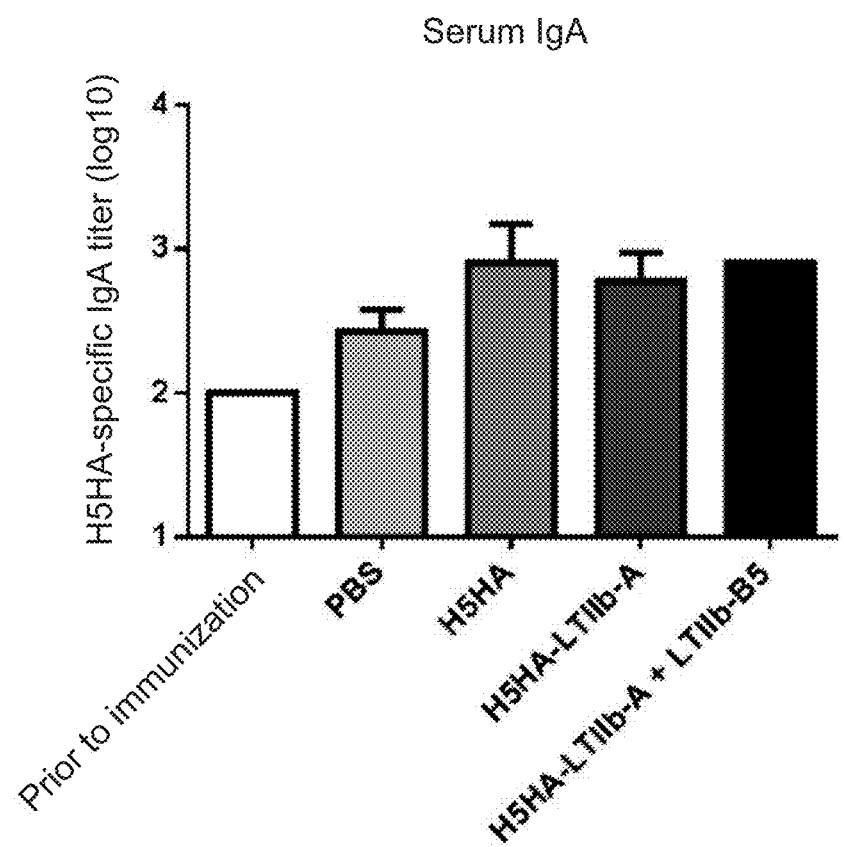

FIG. 8A and FIG. 8B respectively show titers of the anti-recombinant HSHA protein IgY and IgA in chick serum. According to FIG. 8A, immunization with the recombinant HSHA protein slightly increased the serum IgY level as compared to that before immunization, but immunization with the HSHA-LTIIb-A fusion protein significantly increased the IgY level. Similarly, the combination of the HSHA-LTIIb-A fusion protein and the recombinant LTIIb-B5 protein also induced high levels of IgY. According to FIG. 8B, immunization with either the recombinant HSHA protein or the HSHA-LTIIb-A fusion protein led to a slight increase in the serum IgA level as compared to that before immunization. The results indicate that administration of the antigen fusion protein of the present invention to birds significantly increases the level of IgA having specificity for the antigen. Therefore, the antigen fusion protein of the present invention enhances the systemic immune response in birds against the influenza virus antigen.

Example 8

Induction of Influenza Virus Neutralizing Antibodies in Chicken by the H5HA-LTIIb-A Fusion Protein Chicks were immunized differently according to the method described in Example 7, and viral hemagglutinin inhibition assay (HI assay) was used to detect the presence of antibodies in chick serum that inhibited the hemagglutination of H5N1 influenza virus. Also, the titers of serum neutralizing antibodies against H5N1 influenza virus were determined using plaque reduction neutralization test (PRNT). The titer of neutralizing antibodies is defined as the fold of dilution of the serum required to reduce virus infection by 50%.

Figure 9:
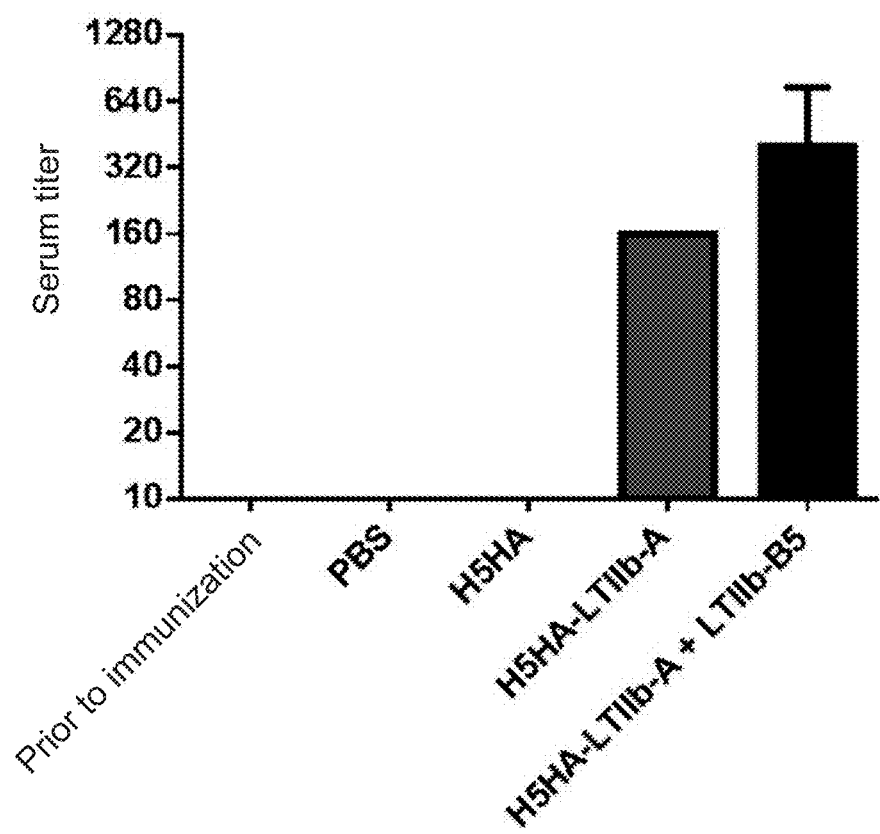
FIG. 9 shows titers of chick antisera that were determined by viral hemagglutinin inhibition assay (HI assay); the antisera were obtained from chicks immunized with PBS, the recombinant HSHA protein, the HSHA-LTIIb-A fusion protein, or the combination of the HSHA-LTIIb-A fusion protein and the recombinant LTIIb-B5 protein.

FIG. 9 shows titers of chick antisera that were determined by HI assay. According to this figure, chick did not produce the hemagglutination-inhibiting antibodies after immunization with the recombinant HSHA protein. However, the hemagglutination induced by H5N1 influenza virus was readily inhibited by the at least 40-fold diluted serum that was obtained after immunization with the HSHA-LTIIb-A fusion protein or the combination of the HSHA-LTIIb-A fusion protein and the recombinant LTIIb-B5 protein. This result indicates that administration of the antigen fusion protein of the present invention effectively induces antibodies in birds that inhibit the action of H5N1 influenza virus.

Figures 10A, 10B:
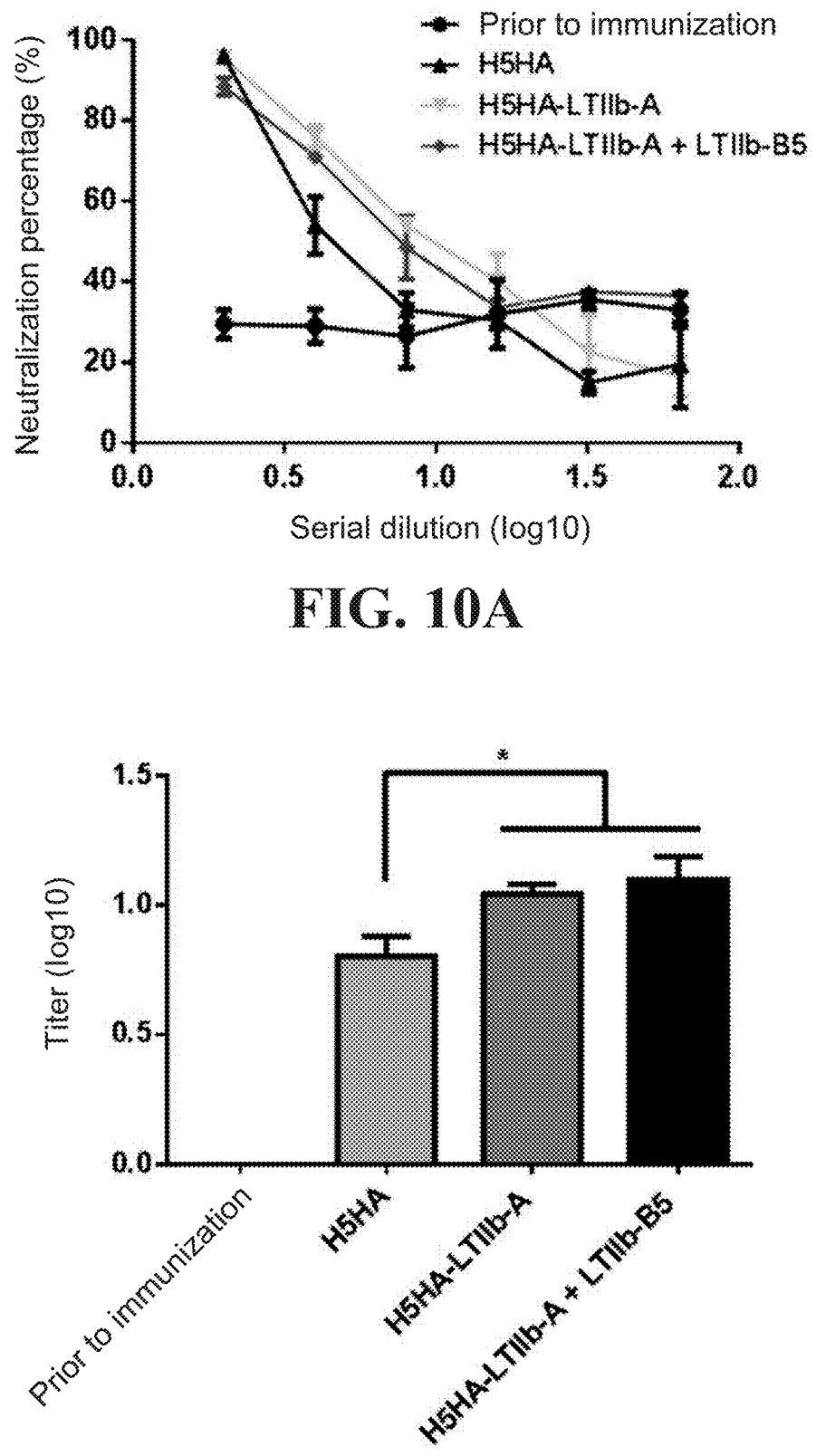

FIG. 10A shows the neutralization curves of H5N1 influenza virus neutralizing antibodies in chick serum. FIG. 10B shows titers of neutralizing antibodies determined based on the data shown in FIG. 10A, where * indicates p<0.05. According to FIG. 10A, the antiserum obtained after immunization with the HSHA-LTIIb-A fusion protein or the combination of the HSHA-LTIIb-A fusion protein and the recombinant LTIIb-B5 protein exhibited higher H5N1 virus neutralizing activity than that obtained after immunization with the recombinant HSHA protein. According to FIG. 10B, the titer of serum neutralizing antibodies elicited by the recombinant HSHA protein was approximately 6.367, the titer of neutralizing antibodies elicited by the HSHA-LTIIb-A fusion protein was approximately 11.09, and the titer of the neutralizing antibodies elicited by the combination of the HSHA-LTIIb-A fusion protein and the recombinant LTIIb-B5 protein was approximately 12.55. The results show that administration of the antigen fusion protein of the present invention elicits significantly more anti-H5N1 influenza virus neutralizing antibodies in birds.

In conclusion, administration (such as intranasal injection) of the influenza mucosal vaccine composition of the present invention to a subject effectively elicits humoral and cellular immune responses against influenza virus, including production of the antigen-specific and influenza virus neutralizing IgG (or IgY) and IgA in blood and bronchoalveolar mucosa as well as cytokines such as IFN-γ, IL-4, and IL-17A secreted by T cells. Thus, the influenza mucosal vaccine composition provides subjects with effective protection against influenza virus infection, such as against infection by the highly pathogenic avian influenza virus H5N1.

Although the present invention has been described with reference to the preferred embodiments, it will be apparent to those skilled in the art that a variety of modifications and changes in form and detail may be made without departing from the scope of the present invention defined by the appended claims.

What is claimed is:

1. An influenza mucosal vaccine composition, comprising an antigen fusion protein, wherein the antigen fusion protein comprises an influenza virus antigen and the Type IIb heat-labile enterotoxin A subunit from *Escherichia coli.*

2. The influenza mucosal vaccine composition of claim 1, wherein the influenza virus antigen is a hemagglutinin ectodomain.

3. The influenza mucosal vaccine composition of claim 1, wherein an N-terminal region of the antigen fusion protein further comprises a poly-histidine segment.

4. The influenza mucosal vaccine composition of claim 1, further comprising a pentameric protein consisting of five copies of the Type IIb heat-labile enterotoxin B subunit from *Escherichia coli.*

5. The influenza mucosal vaccine composition of claim 2, further comprising a pentameric protein consisting of five copies of the Type IIb heat-labile enterotoxin B subunit from *Escherichia coli.*

6. The influenza mucosal vaccine composition of claim 3, further comprising a pentameric protein consisting of five copies of the Type IIb heat-labile enterotoxin B subunit from *Escherichia coli.*

7. The influenza mucosal vaccine composition of claim 2, wherein the antigen fusion protein is in an amount of at least 10 μg.

8. A method of reducing influenza viral infection, comprising administering to a subject in need an influenza mucosal vaccine composition comprising an antigen fusion protein, wherein the antigen fusion protein comprises an influenza virus antigen and the Type IIb heat-labile enterotoxin A subunit from *Escherichia coli.*

9. The method of claim 8, wherein the influenza virus antigen is a hemagglutinin ectodomain.

10. The method of claim 8, wherein an N-terminal region of the antigen fusion protein further comprises a poly-histidine segment.

11. The method of claim 8, wherein the antigen fusion protein activates Toll-like receptor 2/1.

12. The method of claim 8, wherein the antigen fusion protein induces a T-cell related immune response.

13. The method of claim 12, wherein the T-cell related immune response includes secretion of interferon-γ, interleukin-4, interleukin-17A, or any combinations thereof.

14. The method of claim 8, wherein the influenza mucosal vaccine composition further comprises a pentameric protein consisting of five copies of the Type IIb heat-labile enterotoxin B subunit from *Escherichia coli.*

15. The method of claim 8, wherein the influenza mucosal vaccine composition is administered intranasally.

16. A method of preparing an influenza mucosal vaccine composition, comprising the steps of:
   (a) preparing an antigen fusion protein comprising an influenza virus antigen and the Type IIb heat-labile enterotoxin A subunit from *Escherichia coli*; and
   (b) mixing the antigen fusion protein with a pharmaceutically acceptable carrier to obtain the influenza mucosal vaccine composition.

17. The method of claim 16, wherein the influenza virus antigen is a hemagglutinin ectodomain.

18. The method of claim 16, wherein an N-terminal region of the antigen fusion protein further comprises a polyhistidine segment.

19. The method of claim 16, further comprising adding a pentameric protein consisting of five copies of the Type IIb heat-labile enterotoxin B subunit from *Escherichia coli* to the influenza mucosal vaccine composition.

* * * * *

SEQUENCE LISTING

<160> NUMBER OF SEQ ID NOS: 58

<210> SEQ ID NO 1
<211> LENGTH: 11
<212> TYPE: PRT
<213> ORGANISM: Artificial sequence
<220> FEATURE:
<223> OTHER INFORMATION: Cleavage site of H5 hemagglutinin

<400> SEQUENCE: 1

Pro Gln Arg Glu Arg Arg Arg Lys Lys Arg Gly
1               5                   10

<210> SEQ ID NO 2
<211> LENGTH: 7
<212> TYPE: PRT
<213> ORGANISM: Artificial sequence
<220> FEATURE:
<223> OTHER INFORMATION: Substitution sequence for the clevage site of
      H5 hemagglutinin

<400> SEQUENCE: 2

Pro Gln Arg Glu Thr Arg Gly
1               5

<210> SEQ ID NO 3
<211> LENGTH: 300
<212> TYPE: DNA
<213> ORGANISM: Escherichia coli

<400> SEQUENCE: 3
ggagcatctc agttcttcaa agacaattgt aatcgtacca ccgcttctct ggtcgagggt      60
gtagagctga ccaaatatat cagcgacatt aataacaaca ccgacgggat gtatgtagtg     120
agttccacag gcggagtatg gcgtatcagt cgtgccaaag actatccgga taacgtcatg     180
acagccgaaa tgcgcaaaat tgctatggcg gcagttctgt ctggtatgcg cgtgaacatg     240
tgtgctagtc cagcaagttc gcctaacgtg atctgggcca tcgaactgga agcagaataa     300

<210> SEQ ID NO 4
<211> LENGTH: 15
<212> TYPE: PRT
<213> ORGANISM: Artificial sequence

```
<220> FEATURE:
<223> OTHER INFORMATION: H5 hemagglutinin peptide 1

<400> SEQUENCE: 4

Met Glu Lys Ile Val Leu Leu Leu Ala Ile Val Ser Leu Val Lys
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: H5 hemagglutinin peptide 2

<400> SEQUENCE: 5

Leu Ala Ile Val Ser Leu Val Lys Ser Asp Gln Ile Cys Ile Gly
1               5                   10                  15

<210> SEQ ID NO 6
<211> LENGTH: 15
<212> TYPE: PRT
<213> ORGANISM: Artificial sequence
<220> FEATURE:
<223> OTHER INFORMATION: H5 hemagglutinin peptide 3

<400> SEQUENCE: 6

Lys Ser Asp Gln Ile Cys Ile Gly Tyr His Ala Asn Asn Ser Thr
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: H5 hemagglutinin peptide 4

<400> SEQUENCE: 7

Gly Tyr His Ala Asn Asn Ser Thr Glu Gln Val Asp Thr Ile Met
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: H5 hemagglutinin peptide 5

<400> SEQUENCE: 8

Thr Glu Gln Val Asp Thr Ile Met Glu Lys Asn Val Thr Val Thr
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: H5 hemagglutinin peptide 6

<400> SEQUENCE: 9

Met Glu Lys Asn Val Thr Val Thr His Ala Gln Asp Ile Leu Glu
1               5                   10                  15

<210> SEQ ID NO 10
<211> LENGTH: 15
<212> TYPE: PRT
<213> ORGANISM: Artificial sequence
<220> FEATURE:
```

```
<223> OTHER INFORMATION: H5 hemagglutinin peptide 7

<400> SEQUENCE: 10

Thr His Ala Gln Asp Ile Leu Glu Lys Thr His Asn Gly Lys Leu
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: H5 hemagglutinin peptide 8

<400> SEQUENCE: 11

Glu Lys Thr His Asn Gly Lys Leu Cys Asp Leu Asp Gly Val Lys
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: H5 hemagglutinin peptide 9

<400> SEQUENCE: 12

Leu Cys Asp Leu Asp Gly Val Lys Pro Leu Ile Leu Arg Asp Cys
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: H5 hemagglutinin peptide 10

<400> SEQUENCE: 13

Lys Pro Leu Ile Leu Arg Asp Cys Ser Val Ala Gly Trp Leu Leu
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: H5 hemagglutinin peptide 11

<400> SEQUENCE: 14

Cys Ser Val Ala Gly Trp Leu Leu Gly Asn Pro Met Cys Asp Glu
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: H5 hemagglutinin peptide 12

<400> SEQUENCE: 15

Leu Gly Asn Pro Met Cys Asp Glu Phe Ile Asn Val Pro Glu Trp
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: H5 hemagglutinin peptide 13
```

<400> SEQUENCE: 16

Glu Phe Ile Asn Val Pro Glu Trp Ser Tyr Ile Val Glu Lys Ala
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: H5 hemagglutinin peptide 14

<400> SEQUENCE: 17

Trp Ser Tyr Ile Val Glu Lys Ala Asn Pro Val Asn Asp Leu Cys
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: H5 hemagglutinin peptide 15

<400> SEQUENCE: 18

Ala Asn Pro Val Asn Asp Leu Cys Tyr Pro Gly Asp Phe Asn Asp
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: H5 hemagglutinin peptide 16

<400> SEQUENCE: 19

Cys Tyr Pro Gly Asp Phe Asn Asp Tyr Glu Glu Leu Lys His Leu
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: H5 hemagglutinin peptide 17

<400> SEQUENCE: 20

Asp Tyr Glu Glu Leu Lys His Leu Leu Ser Arg Ile Asn His Phe
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: H5 hemagglutinin peptide 18

<400> SEQUENCE: 21

Leu Leu Ser Arg Ile Asn His Phe Glu Lys Ile Gln Ile Ile Pro
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: H5 hemagglutinin peptide 19

```
<400> SEQUENCE: 22

Phe Glu Lys Ile Gln Ile Ile Pro Lys Ser Ser Trp Ser Ser His
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: H5 hemagglutinin peptide 20

<400> SEQUENCE: 23

Pro Lys Ser Ser Trp Ser Ser His Glu Ala Ser Leu Gly Val Ser
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: H5 hemagglutinin peptide 21

<400> SEQUENCE: 24

His Glu Ala Ser Leu Gly Val Ser Ser Ala Cys Pro Tyr Gln Gly
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: H5 hemagglutinin peptide 22

<400> SEQUENCE: 25

Ser Ser Ala Cys Pro Tyr Gln Gly Lys Ser Ser Phe Phe Arg Asn
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: H5 hemagglutinin peptide 23

<400> SEQUENCE: 26

Gly Lys Ser Ser Phe Phe Arg Asn Val Val Trp Leu Ile Lys Lys
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: H5 hemagglutinin peptide 24

<400> SEQUENCE: 27

Asn Val Val Trp Leu Ile Lys Lys Asn Ser Thr Tyr Pro Thr Ile
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: H5 hemagglutinin peptide 25

<400> SEQUENCE: 28
```

Lys Asn Ser Thr Tyr Pro Thr Ile Lys Arg Ser Tyr Asn Asn Thr
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: H5 hemagglutinin peptide 26

<400> SEQUENCE: 29

Ile Lys Arg Ser Tyr Asn Asn Thr Asn Gln Glu Asp Leu Leu Val
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: H5 hemagglutinin peptide 27

<400> SEQUENCE: 30

Thr Asn Gln Glu Asp Leu Leu Val Leu Trp Gly Ile His His Pro
1 5 10 15

<210> SEQ ID NO 31
<211> LENGTH: 15
<212> TYPE: PRT
<213> ORGANISM: Artificial sequence
<220> FEATURE:
<223> OTHER INFORMATION: H5 hemagglutinin peptide 28

<400> SEQUENCE: 31

Val Leu Trp Gly Ile His His Pro Asn Asp Ala Ala Glu Gln Thr
1 5 10 15

<210> SEQ ID NO 32
<211> LENGTH: 15
<212> TYPE: PRT
<213> ORGANISM: Artificial sequence
<220> FEATURE:
<223> OTHER INFORMATION: H5 hemagglutinin peptide 29

<400> SEQUENCE: 32

Pro Asn Asp Ala Ala Glu Gln Thr Lys Leu Tyr Gln Asn Pro Thr
1 5 10 15

<210> SEQ ID NO 33
<211> LENGTH: 15
<212> TYPE: PRT
<213> ORGANISM: Artificial sequence
<220> FEATURE:
<223> OTHER INFORMATION: H5 hemagglutinin peptide 30

<400> SEQUENCE: 33

Thr Lys Leu Tyr Gln Asn Pro Thr Thr Tyr Ile Ser Val Gly Thr
1 5 10 15

<210> SEQ ID NO 34
<211> LENGTH: 15
<212> TYPE: PRT
<213> ORGANISM: Artificial sequence
<220> FEATURE:
<223> OTHER INFORMATION: H5 hemagglutinin peptide 31

<400> SEQUENCE: 34

Thr Thr Tyr Ile Ser Val Gly Thr Ser Thr Leu Asn Gln Arg Leu
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: H5 hemagglutinin peptide 32

<400> SEQUENCE: 35

Thr Ser Thr Leu Asn Gln Arg Leu Val Pro Arg Ile Ala Thr Arg
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: H5 hemagglutinin peptide 33

<400> SEQUENCE: 36

Leu Val Pro Arg Ile Ala Thr Arg Ser Lys Val Asn Gly Gln Ser
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: H5 hemagglutinin peptide 34

<400> SEQUENCE: 37

Arg Ser Lys Val Asn Gly Gln Ser Gly Arg Met Glu Phe Phe Trp
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: H5 hemagglutinin peptide 35

<400> SEQUENCE: 38

Ser Gly Arg Met Glu Phe Phe Trp Thr Ile Leu Lys Pro Asn Asp
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: H5 hemagglutinin peptide 36

<400> SEQUENCE: 39

Trp Thr Ile Leu Lys Pro Asn Asp Ala Ile Asn Phe Glu Ser Asn
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: H5 hemagglutinin peptide 37

<400> SEQUENCE: 40

Asp Ala Ile Asn Phe Glu Ser Asn Gly Asn Phe Ile Ala Pro Glu

```
<210> SEQ ID NO 41
<211> LENGTH: 15
<212> TYPE: PRT
<213> ORGANISM: Artificial sequence
<220> FEATURE:
<223> OTHER INFORMATION: H5 hemagglutinin peptide 38

<400> SEQUENCE: 41

Asn Gly Asn Phe Ile Ala Pro Glu Tyr Ala Tyr Lys Ile Val Lys
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: H5 hemagglutinin peptide 39

<400> SEQUENCE: 42

Glu Tyr Ala Tyr Lys Ile Val Lys Lys Gly Asp Ser Thr Ile Met
1               5                   10                  15

<210> SEQ ID NO 43
<211> LENGTH: 15
<212> TYPE: PRT
<213> ORGANISM: Artificial sequence
<220> FEATURE:
<223> OTHER INFORMATION: H5 hemagglutinin peptide 40

<400> SEQUENCE: 43

Lys Lys Gly Asp Ser Thr Ile Met Lys Ser Glu Leu Glu Tyr Gly
1               5                   10                  15

<210> SEQ ID NO 44
<211> LENGTH: 15
<212> TYPE: PRT
<213> ORGANISM: Artificial sequence
<220> FEATURE:
<223> OTHER INFORMATION: H5 hemagglutinin peptide 41

<400> SEQUENCE: 44

Met Lys Ser Glu Leu Glu Tyr Gly Asn Cys Asn Thr Lys Cys Gln
1               5                   10                  15

<210> SEQ ID NO 45
<211> LENGTH: 15
<212> TYPE: PRT
<213> ORGANISM: Artificial sequence
<220> FEATURE:
<223> OTHER INFORMATION: H5 hemagglutinin peptide 42

<400> SEQUENCE: 45

Gly Asn Cys Asn Thr Lys Cys Gln Thr Pro Met Gly Ala Ile Asn
1               5                   10                  15

<210> SEQ ID NO 46
<211> LENGTH: 15
<212> TYPE: PRT
<213> ORGANISM: Artificial sequence
<220> FEATURE:
<223> OTHER INFORMATION: H5 hemagglutinin peptide 43

<400> SEQUENCE: 46

Gln Thr Pro Met Gly Ala Ile Asn Ser Ser Met Pro Phe His Asn
1               5                   10                  15
```

<210> SEQ ID NO 47
<211> LENGTH: 15
<212> TYPE: PRT
<213> ORGANISM: Artificial sequence
<220> FEATURE:
<223> OTHER INFORMATION: H5 hemagglutinin peptide 44

<400> SEQUENCE: 47

Asn Ser Ser Met Pro Phe His Asn Ile His Pro Leu Thr Ile Gly
1               5                   10                  15

<210> SEQ ID NO 48
<211> LENGTH: 15
<212> TYPE: PRT
<213> ORGANISM: Artificial sequence
<220> FEATURE:
<223> OTHER INFORMATION: H5 hemagglutinin peptide 45

<400> SEQUENCE: 48

Asn Ile His Pro Leu Thr Ile Gly Glu Cys Pro Lys Tyr Val Lys
1               5                   10                  15

<210> SEQ ID NO 49
<211> LENGTH: 15
<212> TYPE: PRT
<213> ORGANISM: Artificial sequence
<220> FEATURE:
<223> OTHER INFORMATION: H5 hemagglutinin peptide 46

<400> SEQUENCE: 49

Gly Glu Cys Pro Lys Tyr Val Lys Ser Asn Arg Leu Val Leu Ala
1               5                   10                  15

<210> SEQ ID NO 50
<211> LENGTH: 15
<212> TYPE: PRT
<213> ORGANISM: Artificial sequence
<220> FEATURE:
<223> OTHER INFORMATION: H5 hemagglutinin peptide 47

<400> SEQUENCE: 50

Lys Ser Asn Arg Leu Val Leu Ala Thr Gly Leu Arg Asn Ser Pro
1               5                   10                  15

<210> SEQ ID NO 51
<211> LENGTH: 15
<212> TYPE: PRT
<213> ORGANISM: Artificial sequence
<220> FEATURE:
<223> OTHER INFORMATION: H5 hemagglutinin peptide 48

<400> SEQUENCE: 51

Ala Thr Gly Leu Arg Asn Ser Pro Gln Arg Glu Arg Arg Arg Lys
1               5                   10                  15

<210> SEQ ID NO 52
<211> LENGTH: 10
<212> TYPE: PRT
<213> ORGANISM: Artificial sequence
<220> FEATURE:
<223> OTHER INFORMATION: H5 hemagglutinin peptide 49

<400> SEQUENCE: 52

Pro Gln Arg Glu Arg Arg Arg Lys Lys Arg
1               5                   10

-continued

<210> SEQ ID NO 53
<211> LENGTH: 23
<212> TYPE: PRT
<213> ORGANISM: Artificial sequence
<220> FEATURE:
<223> OTHER INFORMATION: H5 hemagglutinin peptide 50

<400> SEQUENCE: 53

```
Asp Lys Glu Ser Thr Gln Lys Ala Ile Asp Gly Val Thr Asn Lys Val
1               5                   10                  15

Asn Ser Ile Ile Asp Lys Met
            20
```

<210> SEQ ID NO 54
<211> LENGTH: 263
<212> TYPE: PRT
<213> ORGANISM: Escherichia coli

<400> SEQUENCE: 54

```
Met Ala Lys Val Ile Ser Phe Phe Ile Ser Leu Phe Leu Ile Ser Phe
1               5                   10                  15

Pro Leu Tyr Ala Asn Asp Tyr Phe Arg Ala Asp Ser Arg Thr Pro Asp
            20                  25                  30

Glu Val Arg Arg Ser Gly Gly Leu Ile Pro Arg Gly Gln Asp Glu Ala
        35                  40                  45

Tyr Glu Arg Gly Thr Pro Ile Asn Ile Asn Leu Tyr Asp His Ala Arg
    50                  55                  60

Gly Thr Ala Thr Gly Asn Thr Arg Tyr Asn Asp Gly Tyr Val Ser Thr
65                  70                  75                  80

Thr Thr Thr Leu Arg Gln Ala His Phe Leu Gly Gln Asn Met Leu Gly
                85                  90                  95

Gly Tyr Asn Glu Tyr Tyr Ile Tyr Val Val Ala Ala Ala Pro Asn Leu
            100                 105                 110

Phe Asp Val Asn Gly Val Leu Gly Arg Tyr Ser Pro Tyr Pro Ser Glu
        115                 120                 125

Asn Glu Tyr Ala Ala Leu Gly Gly Ile Pro Leu Ser Gln Ile Ile Gly
    130                 135                 140

Trp Tyr Arg Val Ser Phe Gly Ala Ile Glu Gly Gly Met His Arg Asn
145                 150                 155                 160

Arg Asp Tyr Arg Arg Asp Leu Phe Arg Gly Leu Ser Ala Ala Pro Asn
                165                 170                 175

Glu Asp Gly Tyr Arg Ile Ala Gly Phe Pro Asp Gly Phe Pro Ala Trp
            180                 185                 190

Glu Glu Val Pro Trp Arg Glu Phe Ala Pro Asn Ser Cys Leu Pro Asn
        195                 200                 205

Asn Lys Ala Ser Ser Asp Thr Thr Cys Ala Ser Leu Thr Asn Lys Leu
    210                 215                 220

Ser Gln His Asp Leu Ala Asp Phe Lys Lys Tyr Ile Lys Arg Lys Phe
225                 230                 235                 240

Thr Leu Met Thr Leu Leu Ser Ile Asn Asn Asp Gly Phe Phe Ser Asn
                245                 250                 255

Asn Gly Gly Lys Asp Glu Leu
            260
```

<210> SEQ ID NO 55
<211> LENGTH: 1731
<212> TYPE: DNA

<213> ORGANISM: Influenza A virus

<400> SEQUENCE: 55

```
atggagaaaa tagtgcttct tttgcaata gtcagtcttg ttaaaagtga tcagatttgc      60
attggttacc atgcaaacaa ctcgacagag caggttgaca caataatgga aaagaacgtt    120
actgttacac atgcccaaga catactggaa aagacacaca acgggaagct ctgcgatcta    180
gatggagtga agcctctaat tttgagagat tgtagtgtag ctggatggct cctcggaaac    240
ccaatgtgtg acgaattcat caatgtgccg gaatggtcct acatagtgga gaaggccaat    300
ccagtcaatg acctctgtta cccaggggat ttcaatgact atgaagaatt gaaacaccta    360
ttgagcagaa taaaccattt tgagaaaatt cagatcatcc ccaaaagttc ttggtccagt    420
catgaagcct cattaggggt gagctcagca tgtccatacc agagaaagtc ctcctttttc    480
agaaatgtgg tatggcttat caaaaagaac agtacatacc caacaataaa gaggagctac    540
aataatacca accaagaaga tcttttggta ctgtgggggga ttcaccatcc taatgatgcg    600
gcagagcaga caaagctcta tcaaaaccca accacctata tttccgttgg gacatcaaca    660
ctaaaccaga gattggtacc aagaatagct actagatcca aagtaaacgg gcaaagtgga    720
aggatggagt tcttctggac aattttaaaa ccgaatgatg caatcaactt cgagagtaat    780
ggaaatttca ttgctccaga atatgcatac aaaattgtca agaaagggga ctcaacaatt    840
atgaaaagtg aattggaata tggtaactgc aacaccaagt gtcaaactcc aatgggggcg    900
ataaactcta gtatgccatt ccacaatata caccctctca ccatcgggga atgccccaaa    960
tatgtgaaat caaacagatt agtccttgcg actgggctca gaaatagccc tcaaagagag   1020
accagaggat tatttggagc tatagcaggt tttatagagg gaggatggca gggaatggta   1080
gatggttggt atgggtacca ccatagcaat gagcagggga gtgggtacgc tgcagacaaa   1140
gaatccactc aaaaggcaat agatggagtc accaataagg tcaactcgat cattgacaaa   1200
atgaacactc agtttgaggc cgttggaagg gaatttaaca acttagaaag gagaatagag   1260
aatttaaaca agaagatgga agacgggttc ctagatgtct ggacttataa tgctgaactt   1320
ctggttctca tggaaaatga gagaactcta gactttcatg actcaaatgt caagaacctt   1380
tacgacaagg tccgactaca gcttagggat aatgcaaagg aactgggtaa cggttgtttc   1440
gagttctatc ataaatgtga taatgaatgt atggaaagtg taagaaacgg aacgtatgac   1500
tacccgcagt attcagaaga agcaagacta aaaagagagg aaataagtgg agtaaaattg   1560
gaatcaatag gaatttacca aagcggccgc ctggtgccgc gcggcagccc gatgaaacag   1620
attgaagata aaattgaaga aattctgagc aaaatttatc atattgaaaa cgaaattgcg   1680
cgcattaaaa aactgattgg cgaagtgggc catcatcatc atcatcatta a            1731
```

<210> SEQ ID NO 56
<211> LENGTH: 732
<212> TYPE: DNA
<213> ORGANISM: Escherichia coli

<400> SEQUENCE: 56

```
aacgattatt ttcgtgcgga tagccgtacc ccggatgaag tgcgtcgtag cggcggcctg      60
attccgcgtg gccaggatga agcgtatgaa cgtggcaccc cgattaacat taacctgtat    120
gatcatgcgc gtggcaccgc gaccggcaac acccgttata acgatggcta tgtgagcacc    180
accaccaccc tgcgtcaggc gcattttctg ggccagaaca tgctgggcgg ctataacgaa    240
tattatattt atgtggtggc ggcggcgccg aacctgtttg atgtgaacgg cgtgctgggc    300
```

-continued

```
cgttatagcc cgtatccgag cgaaaacgaa tatgcggcgc tgggcggcat tccgctgagc    360
cagattattg gctggtatcg tgtgagcttt ggcgcgattg aaggcggcat gcatcgtaac    420
cgtgattatc gtcgtgatct gtttcgtggc ctgagcgcgg cgccgaacga agatggctat    480
cgtattgcgg gctttccgga tggctttccg gcgtgggaag aagtgccgtg gcgtgaattt    540
gcgccgaaca gctgcctgcc gaacaacaaa gcgagcagcg ataccacctg cgcgagcctg    600
accaacaaac tgagccagca tgatctggcg gattttaaaa aatatattaa acgtaaattt    660
accctgatga ccctgctgag cattaacaac gatggctttt ttagcaacaa cggcggcaaa    720
gatgaactgt aa                                                        732
```

<210> SEQ ID NO 57
<211> LENGTH: 43
<212> TYPE: PRT
<213> ORGANISM: Artificial sequence
<220> FEATURE:
<223> OTHER INFORMATION: GCN4 leucine zipper

<400> SEQUENCE: 57

```
Ser Gly Arg Leu Val Pro Arg Gly Ser Pro Met Lys Gln Ile Glu Asp
1               5                   10                  15

Lys Ile Glu Glu Ile Leu Ser Lys Ile Tyr His Ile Glu Asn Glu Ile
            20                  25                  30

Ala Arg Ile Lys Lys Leu Ile Gly Glu Val Gly
        35                  40
```

<210> SEQ ID NO 58
<211> LENGTH: 8
<212> TYPE: PRT
<213> ORGANISM: Artificial sequence
<220> FEATURE:
<223> OTHER INFORMATION: GS linker

<400> SEQUENCE: 58

```
Gly Gly Ser Gly Gly Gly Ser Gly
1               5
```